US010471161B2

(12) United States Patent
Li et al.

(10) Patent No.: US 10,471,161 B2
(45) Date of Patent: Nov. 12, 2019

(54) VINYLSULFONE-BASED 18F-LABELING COMPOSITIONS AND METHODS AND USES THEREOF

(71) Applicants: University of Southern California USC Stevens, Los Angeles, CA (US); City of Hope, Duarte, CA (US)

(72) Inventors: Zibo Li, Logan, UT (US); Peter S. Conti, Pasadena, CA (US); Lin Li, Los Angeles, CA (US); Zhanhong Wu, Los Angeles, CA (US); Shuanlong Liu, Alhambra, CA (US); John E. Shively, Los Angeles, CA (US); David Horne, Los Angeles, CA (US)

(73) Assignees: University of Southern California, Los Angeles, CA (US); City of Hope, Duarte, CA (US)

( * ) Notice: Subject to any disclaimer, the term of this patent is extended or adjusted under 35 U.S.C. 154(b) by 0 days.

(21) Appl. No.: 14/773,733

(22) PCT Filed: Mar. 8, 2014

(86) PCT No.: PCT/US2014/022200
§ 371 (c)(1),
(2) Date: Sep. 8, 2015

(87) PCT Pub. No.: WO2014/138720
PCT Pub. Date: Sep. 12, 2014

(65) Prior Publication Data
US 2016/0015838 A1   Jan. 21, 2016

(51) Int. Cl.
*A61K 51/00* (2006.01)
*A61K 51/04* (2006.01)
*C07K 1/13* (2006.01)
*A61K 51/08* (2006.01)
*C07C 317/18* (2006.01)
*C07K 7/08* (2006.01)
*C07K 7/64* (2006.01)

(52) U.S. Cl.
CPC .......... *A61K 51/0497* (2013.01); *A61K 51/04* (2013.01); *A61K 51/082* (2013.01); *A61K 51/084* (2013.01); *A61K 51/085* (2013.01); *A61K 51/088* (2013.01); *C07C 317/18* (2013.01); *C07K 1/13* (2013.01); *C07K 7/083* (2013.01); *C07K 7/64* (2013.01); *C07B 2200/05* (2013.01)

(58) Field of Classification Search
None
See application file for complete search history.

(56) References Cited

U.S. PATENT DOCUMENTS

| 5,414,135 A | 5/1995 | Snow et al. |
| 5,747,639 A * | 5/1998 | Seely ............. A61K 47/60 |
| | | 210/198.2 |
| 2005/0191240 A1 | 9/2005 | Srinivasan et al. |
| 2008/0139787 A1 | 6/2008 | De Jesus et al. |
| 2010/0196270 A1* | 8/2010 | Cuthbertson ........ A61K 51/088 |
| | | 424/1.69 |
| 2011/0092678 A1 | 4/2011 | Gonzalez et al. |
| 2011/0160430 A1 | 6/2011 | de Jesus et al. |
| 2012/0207676 A1 | 8/2012 | Gruaz-Guyon et al. |

FOREIGN PATENT DOCUMENTS

| CN | 1768266 A | 5/2006 |
| CN | 101854957 A | 10/2010 |
| CN | 101903439 A | 12/2010 |
| JP | 2001-506587 A | 5/2001 |
| WO | 2004079370 A1 | 9/2004 |
| WO | 2005009928 A2 | 2/2005 |
| WO | 2009153577 A1 | 12/2009 |

OTHER PUBLICATIONS

Kol, Moshe et al, "Isolation and characterization of methyl hypofluorite." J. Am. Chem. Soc. (1991) 113 p. 2648-2651.*
Solomons, T. W. Graham, "Organic Chemistry" (1988) ISBN 0-471-83659-1.*
Hultsch et al. "Radiolabeling of multimeric neurotensin (8-13) analogs with the short-lived positron emitter fluorine-18", Applied Radiation and Isotopes, 2007, vol. 65, pp. 818-826 [Downloaded from: www.sciencedirect.com] Abstract; p. 824, col. 1, para 2—col. 2, para 3; Fig 4; Table 4.
Supplementary European Search Report dated Oct. 14, 2016 issued in counterpart European Patent Application No. 14760051.
Bogyo, et al.: "Covalent modification of the active site threonine of proteasomal beta subunits and the *Escherichia coli* homolog Hs1V by a new class of inhibitors", Proceedings of the National Academy of Sciences, National Academy of Sciences, US, vol. 94, No. 13, Jan. 1, 1997, pp. 6629-6634.
Morales-Sanfrutos, et al.: "Vinyl Sulfone Bifunctional Tag Reagents for Single-Point Modification of Proteins", The Journal of Organic Chemistry, vol. 75, No. 12, May 24, 2010, pp. 4039-4047.
English translation of Chinese Search Report dated Aug. 4, 2016, issued in counterpart Chinese Patent Application No. 201480026107.1.
Gambhir, S., "New Gene Based Probes for Imaging Breast Cancer with PET", Aug. 2001.
English translation of the First Office Action dated May 9, 2017 (dated May 9, 2017), in corresponding Japanese Application No. 2015-561748, pp. 1-4.

(Continued)

*Primary Examiner* — Fred H Reynolds
(74) *Attorney, Agent, or Firm* — DLA Piper LLP (US)

(57) ABSTRACT

A thio-selective radioactive labeling agent has the following general formula:

*R-L-VS, wherein said *R is a radioisotope, L is a linking group, and VS is a vinylsulfone functional group.

6 Claims, 16 Drawing Sheets

(56) References Cited

OTHER PUBLICATIONS

Frank Wuest et al., "Systematic comparison of two novel, thiol-reactive prosthetic groups for 18F labeling of peptides and proteins with the acylation agent succinimidyl-4-[18F]fluorobenzoate ([18F]SFB)", Amino Acids, 2009, vol. 36, No. 2, pp. 283-295.

Dong Wook Kim et al., "Recent Trends in the Nucleophilic [18F]-radiolabeling Method with No-carrier-added [18F] fluoride", Nuclear Medicine and Molecular Imaging, 2010, vol. 44, No. 1, pp. 25-32.

Lin Li et al., "Site-Specific Conjugation of Monodispersed DOTA-PEGn to a Thiolated Diabody Reveals the Effect of Increasing PEG Size on Kidney Clearance and Tumor Uptake with Improved 64-Copper PET Imaging", Bioconjuate Chemistry, 2011, vol. 22, No. 4, pp. 709-716.

Lin Li et al., "Vinyl Sulfone Bifunctional Derivatives of DOTA Allow Sulfhydrylor Amino-Directed Coupling to Antibodies. Conjugates Retain Immunoreactivity and Have Similar Biodistributions", Bioconjugate Chemistry, 2002, vol. 13, pp. 110-115.

Zhanhong Wu et al., "In Vivo Imaging of Transplanted Islets with 64Cu-DO3A-VS-Cys40-Exendin-4 by Targeting GLP-1 Receptor", Bioconjugate Chemistry, 2011, vol. 22, No. 8, pp. 1587-1594.

Lin Li et al., "A Versatile Bifunctional Chelate for Radiolabeling Humanized Anti-CEA Antibody with In-111 and Cu-64 at Either Thiol or Amino Groups: PET Imaging of CEA-Positive Tumors with Whole Antibodies", Bioconjugate Chemistry, 2008, vol. 19, No. 1, pp. 89-95.

Japanese Office Action dated May 9, 2017, regarding JP 2015-561748, with English translation.

Japanese Office Action dated Apr. 24, 2018, regarding JP 2015-551748.

Li, Ian et al.: *"Reduction of Kidney Uptake in Radiometal Labeled Peptide Linkers Conjugated to Recombinant Antibody Fragments. Site-Specific Conjugation of DOTA-Peptides to a Cys-Diabody"*; Bioconjugate Chemistry, 2002, vol. 13, No. 5, p. 985-995.

* cited by examiner

VINYLSULFONE-BASED 18F-LABELING COMPOSITIONS AND METHODS AND USES THEREOF

FIELD OF THE INVENTION

The present invention relates generally to the field of positron emission tomography (PET) imaging. More particularly, the present invention relates to tracers for use in PET imaging and methods for manufacturing said tracers.

BACKGROUND OF THE INVENTION

The positron-emitter fluorine-18 is an ideal radionuclide for the preparation of labeled bioactive peptides and small proteins for low-molecular-weight radiotracers and radiopharmaceuticals due to its physical and nuclear characteristics. Fluorine-18 decays with a high positron abundance (99%). Compared with carbon-11, oxygen-15, and nitrogen-13, the lowest positron emission energy of fluorine-18 (maximum 635 keV) and the shortest positron linear range in tissue (2.3 mm) provide the highest resolution in PET imaging. Its relative long half-life (109.8 min) allows multi-step synthetic approaches, extended imaging protocols over a few hours, kinetic studies and metabolite analysis.

Nearly all prior art fluorine-18 labeling reagents are designed for coupling to the peptide or protein via an amino function. For example, the activated ester N-succinimidyl 4-[$^{18}$F]fluorobenzoate ($^{18}$F-SFB) is one of the most popular agents for introducing prosthetic groups to label peptides and proteins. It does so via an acylation reaction (2-4). Besides $^{18}$F-SFB, $^{18}$F-labeled carboxylic acid and amino reagents are also known. However, they are mainly used in conjunction with the conjugation of amino and carboxylic acid groups in biomaterials of interest (5-10), not in PET probe design and synthesis. One major drawback of these prior art $^{18}$F-labeled agents is that the amino and the carboxyl functions are ubiquitous in proteins, hence, there is no opportunity for selective labeling.

In view of the above, there still exists a need for new labeling methods and agents that are capable of selectively labeling proteins or peptides of interest.

SUMMARY OF THE INVENTION

Accordingly, it is one object of the present invention to provide a chemo-selective method for radio-labeling a compound useful as a PET tracer.

It is also an object of the present invention to provide novel PET tracers with desirable physiological properties for use in PET imagining.

In considering the objects of the present invention, it is recognized in the art that the free thiol function is not as common as amino and carboxylic acid in most peptides and proteins. Therefore, thiol reactive agents have been used to modify peptides and proteins at specific sites, providing a means of higher chemo-selectivity in contrast to the carboxylate and amine-reactive reagents. In 1989, Shiue et al pioneered the development of thiol-reactive agents using $^{18}$F-labeled N-substituted maleimides as a Michael acceptor. N-(p-$^{18}$F-fluorophenyl)-maleimide and m-maleimido-N-(p-$^{18}$F-fluorobenzyl)-benzamide (11) were synthesized for a Fab protein (from rabbit IgG) labeling at the cysteine position. Following this research, three new approaches based on $^{18}$F-labeled N-substituted maleimides as thiol-selective agents were reported. In 2003, Toyokuni et al. developed N-[4-[(4-$^{18}$F-fluorobenzylidene)aminooxy]butyl]maleimide ($^{18}$F-FBABM) (12) as a thiol-reactive agent (FIG. 1A). A thiol-containing tripeptide glutathione was conjugated with $^{18}$F-FBABM affording about 70% decay-corrected radiochemical yield (RCY) at room temperature in 10 min without optimizing the reaction conditions. In 2005, de Bruin et al. reported another 18F-maleimide agent, 1-[3-(2-($^{18}$F-fluoropyridin-3-yloxy)propyl]pyrrole-2,5-dione ($^{18}$F-FpyME) (FIG. 1B). $^{18}$F-FpyME (13) is synthesized in three consecutive steps starting with [3-(3-Boc-aminopropoxy)pyridine-2-yl]trimethylammonium triflate. The overall reaction time is within 110 min with 28-37% decay corrected RCYs. This thiol-reactive agent was applied in the labeling of two 8 kDa thiol-containing proteins, affording 60-70% isolated yield (non-decay corrected). In 2006, Cai et al. synthesized N-[2-(4-$^{18}$F-fluorobenzamido)ethyl]maleimide ($^{18}$F-FBEM) (FIG. 10). $^{18}$F-FBEM (14) was obtained by coupling $^{18}$F-SFB with N-(2-aminoethyl)maleimide. After HPLC purification, the thiol-reactive agent was allowed to react with thiol-containing RGD peptide monomer and dimer at room temperature for 20 min. The overall decay-corrected ROY is 20±4% (n=5) for both RGD monomer and dimer.

Despite the initial success of the above described prior art thiol-reactive labeling agents, the multiple step labeling reactions, complicated procedures, and relatively low yield have limit application of these agents. Thus, prior art radiolabeled thiol-reactive agents still left much to be desired.

To overcome the above difficulties of the prior art, the inventors of the present invention have invented a new approach of radio-labeling thiol-reactive agents involving new types of reagents and methods for manufacturing the same.

One aspect of the present invention is a $^{18}$F labeling method for site specific labeling a free thiol group present or introduced into peptide or proteins. Using this novel method, a NTR1 targeted PET imaging agent was synthesized, that demonstrated specific tumor uptake and superior tumor to background contrast. The elevated tumor to major organ uptake ratios (including tumor/kidney) lead to high contrast images at early time-points post injection. The very low background in normal tissues should allow the detection of very small tumors (especially at the abdomen area) by PET imaging $^{18}$F-DEG-VS-NT.

Thus, one aspect of the invention is directed to a new class of radioactive labeling agents capable of chemo-selectively labeling a target compound. Radioactive labeling agents in accordance with this aspect of the invention will generally include a vinylsulfone functional group and a radioactive labeling isotope having the general formula *R-L-VS, wherein *R is a radioactive isotope, L is a linking group, and VS stands for the vinylsulfone functional group.

The *R radio isotope may be any suitable radio-isotope known in the art. Exemplary radio-isotopes may be I, C, F, Br, but not limited thereto. In one preferred embodiment, the radio-isotope is $^{18}$F. This preferred embodiment is also referred to herein as $^{18}$F vinylsulfone or $^{18}$F-VS.

The linking group L may be any suitable molecular scaffold having functional moieties capable of hosting the vinylsulfone functional group and the R* radio-labeling. Exemplary linking groups may be selected from aromatic, aliphatic, PEG, linker containing heteroatoms, but are not limited thereto.

Another aspect of the invention is directed to methods for selectively labeling a protein or a peptide with a radioactive label. Methods in accordance with this aspect of the invention will generally include the steps of attaching a target protein or peptide with a vinylsulfone radioactive labeling agent as described above. In some embodiments, a step of providing or synthesizing the radioactive labeling agent may be performed shortly before the attaching step. Those skilled in the art will readily recognized that the time period before the providing or synthesizing step may be limited by the half-life of the particular *R label used. With radioactive labels having shorter useful half-lives, the time lag between synthesis and attachment of the *R-VS labeling agent to the target protein/peptide and their ultimate use may be short. In such instances, attachment of the radioactive group must occur within a short period prior to use of the labeled protein/peptide, requiring an on-site system of performing the labeling method. In other instances where the half-life of the *R label is long, labeling of the target protein/peptide may be performed off-site in a mass-production setting, and the resulting labeled protein/peptide be delivered in a packaged format.

Proteins and peptides that are suitable for labeling by the vinylsulfone labeling agents described above will generally include at least one cysteine residue or a free thio-reactive functional group capable of reacting with the vinylsulfone group of the label to form a stable attachment. In some embodiment, the attachment is via formation of a covalent thio-ester bond. In other embodiments, attachment may be via non-covalent attachment. Preferably, the target protein/peptide has between 1 to 10 free thiol-reactive groups and/or cysteine residues. More preferably, the target protein/peptide also has a biological function such as an enzymatic substrate or a structural element involved in certain pathogenic pathways. In a preferred embodiment, the target protein/peptide is neurotensin or a variant thereof, or a thiolated neurotensin variant, other stabilized neurotensin, multimeric neurotensin, heteromeric neurotensin with other ligands. In a more preferred embodiment, the labeling radioactive isotope is $^{18}F$. Even more preferably, the radioactive labeling agent is $^{18}F$-DEG-VS and the targeted peptide is neurotensin $^{18}F$-DEG-VS-NT). Such radio-labeled proteins or peptides may be useful as tracers in imaging techniques such as positron emission tomography (PET).

Still another aspect of the invention is directed to methods of performing PET imaging utilizing novel tracers of the present invention as described above.

Methods in accordance with this aspect of the invention will generally include the steps of administering to a subject an effective amount of a $^{18}F$-VS labeled tracer compound; and imaging the subject with a PET imaging instrument at locations of interest.

Methods for administering the tracer compound is generally known in the art, which may include, but not limited to intravenous injection, oral administration, or any other modes of administration known in the art.

$^{18}F$ vinylsulfone has at least the following advantages over 18F labeled maleimide: 1) One-step $^{18}F$-fluorination precursor to achieve $^{18}F$ vinylsulfone; 2) The product of the reaction of a thiol with a vinylsulfone gives a single stereoisomer structure, unlike conjugation with maleimides, which produces two potential stereoisomers; and 3) these vinylsulfone groups are stable in aqueous solution for extended periods, as they are not subject to hydrolysis at neutral pH (15). Thus, they retain excellent coupling potential for thiol-containing proteins or other molecules even when used in aqueous buffer conditions.

A further aspect of the invention is directed to systems and apparatuses for imaging biological or physiological processes by utilizing the radioactive tracers described above. FIG. 7 shows an exemplary schematics of the system/apparatus in accordance with this aspect of the invention.

Embodiments in accordance with this aspect of the invention may include traditional automated or semi-automated box, microwave reactor, or microfluoidic reactor, or equivalents thereof.

Other features, objects, and advantages of the invention will be apparent from the description and the accompanying drawings, and from the appended claims.

DETAILED DESCRIPTION

Definitions

Figure 1A:
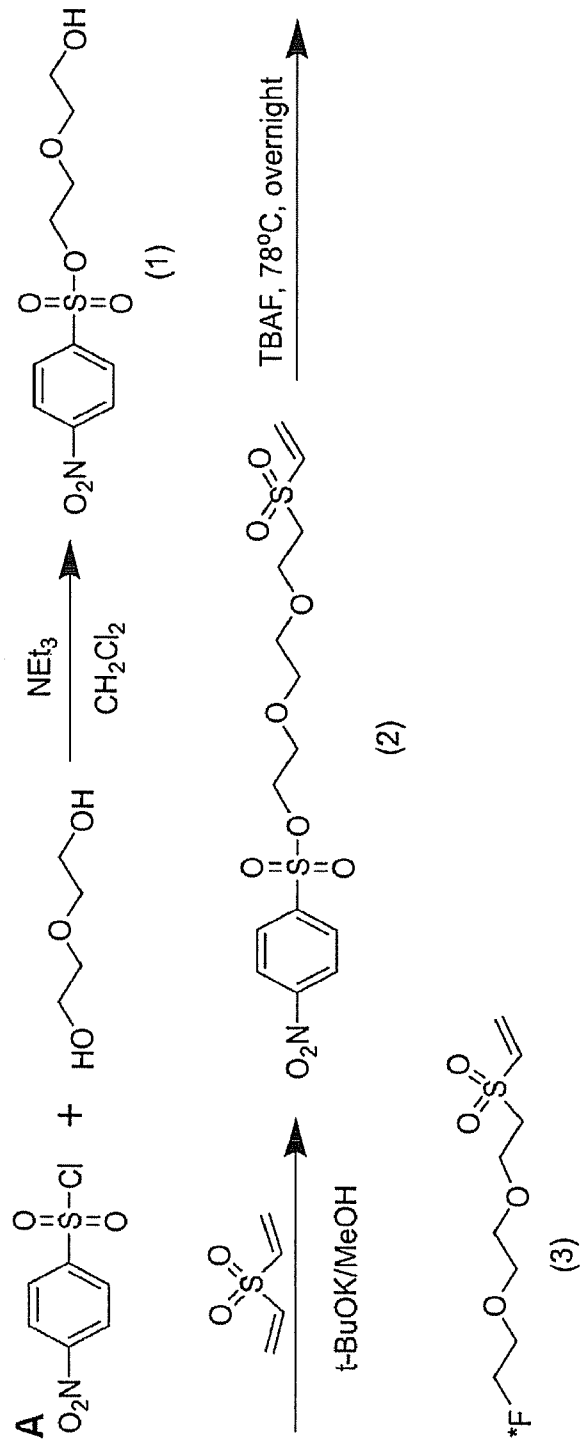
FIG. 1 shows exemplary synthetic scheme and HPLC profile of an 18F-labeled compound in accordance with embodiments of the present invention. (A) Synthetic scheme of F-DEG-VS; (B) HPLC profile of crude reaction of $^{18}F$-DEG-VS. (C) HPLC profile of $^{18}F$-DEG-VS enriched.

Unless otherwise defined, all technical and scientific terms used herein have the same meaning as commonly understood by one of ordinary skill in the art to which this invention pertains. In case of conflict, the present document, including definitions, will control. All publications, patent applications, patents and other references mentioned herein are incorporated by reference in their entirety. The materials, methods, and examples disclosed herein are illustrative only and not intended to be limiting.

As used herein, the term "amino acid" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4-tetrahydroisoquinoline-3-carboxylic acid; penicillamine; ornithine; citruline; a-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a ($C_1$ $C_6$)alkyl, phenyl or benzyl ester or amide). Other suitable amino and carboxy protecting groups are known to those skilled in the art (See for example, T. W. Greene, Protecting Groups In Organic Synthesis; Wiley: New York, 1981; D. Voet, Biochemistry, Wiley: New York, 1990; L. Stryer, Biochemistry, (3rd Ed.), W. H. Freeman and Co.: New York, 1975; J. March, Advanced Organic Chemistry, Reactions, Mechanisms and Structure, (2nd Ed.), McGraw Hill: New York, 1977; F. Carey and R. Sundberg, Advanced Organic Chemistry, Part B: Reactions and Synthesis, (2nd Ed.), Plenum: New York, 1977; and references cited therein). According to the invention, the amino or carboxy protecting group can also comprise a radionuclide (e.g., Fluorine-18, Iodine-123, or Iodine-124).

As used herein, the term "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

The term "polypeptide" refers to a biopolymer compound made up of a single chain of amino acid residues linked by peptide bonds. The term "protein" as used herein may be synonymous with the term "polypeptide" or may refer, in addition, to a complex of two or more polypeptides.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "% homology" is used interchangeably herein with the term "% identity" and refers to the level of nucleic acid Or amino acid sequence identity between two or more aligned sequences, when aligned using a sequence alignment program. For example, 70% homology means the same thing as 70% sequence identity determined by a defined algorithm, and accordingly a homologue of a given sequence has greater than 80% sequence identity over a length of the given sequence. Exemplary levels of sequence identity include, but are not limited to, 80, 85, 90 or 95% or more sequence identity to a given sequence, e.g., the coding sequence for lactoferrin, as described herein As used herein, the term "aptamer," refers to oligonucleic or oligopeptide molecules that bind to a specific target molecule. e.g., RNA aptamer or DNA aptamer, includes single-stranded oligonucleotides that bind specifically to a target molecule.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

The term "alkyl" herein used means $C_1$-$C_{10}$ straight or branched chain alkyl, for example, methyl, ethyl, n-propyl, i-propyl, n-butyl, i-butyl, sec-butyl, tert-butyl, n-pentyl, i-pentyl, neo-pentyl, tert-pentyl, and the like.

The term "alkenyl" refers to a branched or unbranched hydrocarbon having at least one carbon-carbon double bond. The term "C2-7-alkenyl" refers to a hydrocarbon having two to seven carbon atoms and comprising at least one carbon-carbon double bond.

The term "aryl" herein used means monocyclic or condensed ring aromatic hydrocarbons. Examples of the aryl are phenyl, naphthyl, and the like.

The term "heteroaryl" herein used means a 5 to 6 membered aromatic heterocyclic group which contains one or more hetero atoms selected from the group consisting of nitrogen, oxygen and sulfur atoms in the ring and may be fused with a carbocyclic ring or other heterocyclic ring at any possible position.

The term "cycloalky" herein refers to a C3-C8 cycloalkyl exemplified by cyclopropyl, cyclobutyl, cyclopentyl, cyclohexyl, cycloheptyl, and the like One aspect of the present invention is directed to a new class of radioactive labeling agents capable of chemoselectively labeling a target compound. Radioactive labeling agents in accordance with this aspect of the invention will generally include a vinylsulfone functional group and a radioactive labeling isotope and may be represented schematically as having the general formula:

*R-L-VS wherein *R is a radioactive isotope, L is a linking group, and VS stands for the vinylsulfone functional group.

The *R radioisotope may be any suitable radioisotope known in the art, preferably a radioisotope useful in connection with medical imaging applications. Exemplary radioisotopes include but are not limited to, radio-isotopes of I, C, F, Br. In one preferred embodiment, the radio-isotope is $^{18}F$. This preferred embodiment is also referred to herein as $^{18}F$ vinylsulfone or $^{18}F$-VS.

The linking group L may be any suitable molecular scaffold having functional moieties capable of hosting the vinylsulfone functional group and the *R radio-labeling. Exemplary linking groups may be selected group consisting of an aromatic, aliphatic, a polythylend glycol (PEG), a linker containing heteroatoms, but are not limited thereto.

In a preferred embodiment, the linking group is based on a PEG having the general formula:

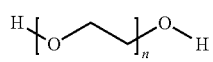

Where n is between 1 and 20, inclusive, preferably between 1 and 10, inclusive and more preferably between 1 and 5, inclusive.

Specific examples of PEG useful as linking groups in connection with the present invention are

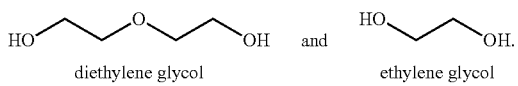

Diethylene Glycol herein is referred to as DEG.

When used in linking groups, the PEG compounds may be modified to contain a functional group, LG, that may be selectively radiolabeled, having the general formula:

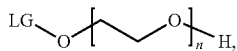

wherein LG is a functional group that may be selectively substituted with a radioisotope, preferably $^{18}F$, and
wherein n is between 1 and 20, inclusive, preferably between 1 and 10, inclusive and more preferably between 1 and 5, inclusive.

For instance, the selected PEG may be reacted 4-Nitrobenzene sulfonyl chloride to provide a -4-nitrobenensulfonate of the following general formula:

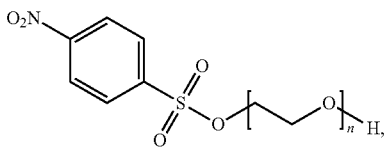

wherein n is between 1 and 20, inclusive, preferably between 1 and 10, inclusive and more preferably between 1 and 5, inclusive.

Although here, the selected functional group LG is a 4-Nitrobenzene sulfonyl group, the identity of the functional group LG1 is not particularly limited and may be selected in accordance with the selected linking group and radiolabel using the guidance disclosed herein.

Suitable vinylsulfones useful in connection with the present invention have the general structure:

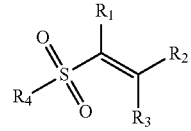

wherein $R_1$, $R_2$, and $R_3$ are independently selected from the group consisting of H, alkyl, cycloalkyl, aryl, and heteroaryl. Further, $R_1$ and $R_2$ may be optionally substituted so as to form a $C_3$-$C_8$ cyclic unsaturated ring. The selected alkyl, cycloalkyl, aryl and heteroaryls may be optionally substituted. $R_4$ is selected from the group consisting be an alkenyl, aryl, heteroaryl, each of which may be optionally substituted.

Further, $R_4$ and $R_3$ may be optionally substituted in order to produce a thio heterocyclic ring system having a 3 to 8 membered ring (inclusive).

In a preferred embodiment, the vinylsulfone has the following structure:

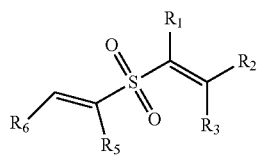

and more preferably

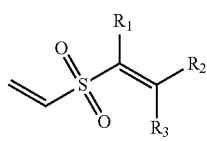

wherein $R_1$, $R_2$, and $R_3$ are independently selected from the group consisting of H, alkyl, cycloalkyl, aryl, and heteroaryl. Further, $R_1$ and $R_2$ may be optionally substituted so as to form a $C_3$-$C_8$ cyclic unsaturated ring, and $R_5$, $R_6$ are independently selected from the group consisting of H, alkyl, cycloalkyl, aryl, and heteroaryl. Further, $R_5$ and $R_6$ may be optionally substituted.

More specifically, the preferred vinylsulfone has the following structure:

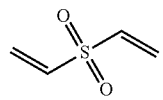

Other exemplary vinylsulfones useful in accordance with respect to the present invention include:

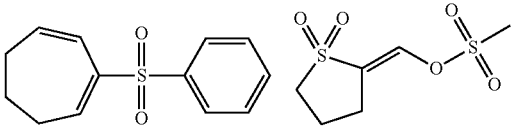

-continued

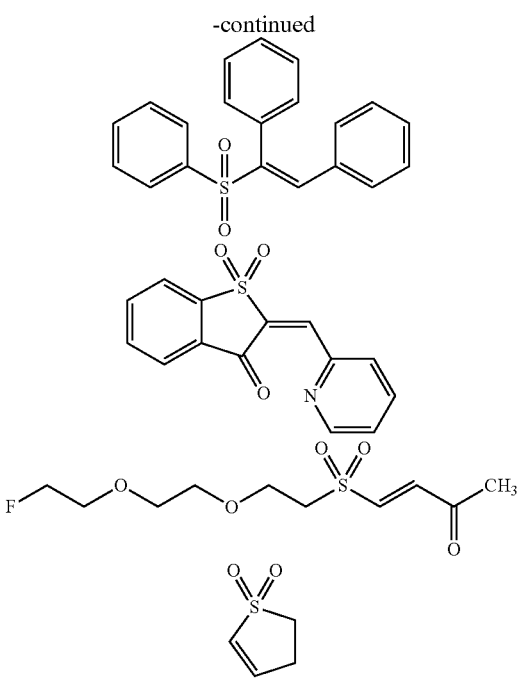

The linker, generally including the functional group LG1 may then be conjugated to form a L-VS conjugate. A preferred embodiment of the L-VS conjugate has the general formula:

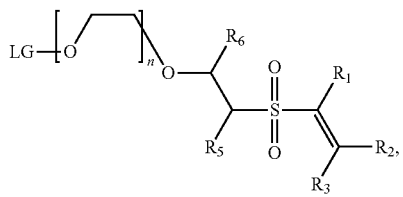

or, in a preferred embodiment,

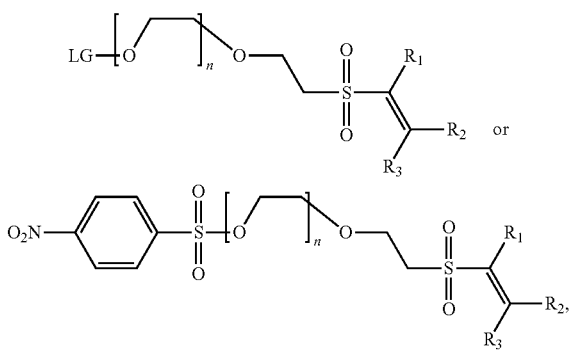

wherein LG is a functional group that may be selectively substituted with a radioisotope, preferably $^{18}$F, and wherein n is between 1 and 20, inclusive, preferably between 1 and 10, inclusive and more preferably between 1 and 5, inclusive $R_1$, $R_2$, and $R_3$ are independently selected from the group consisting of H, alkyl, cycloalkyl, aryl, and heteroaryl. Further, $R_1$ and $R_3$ may be optionally substituted so as to form a $C_3$-$C_8$ cyclic unsaturated ring. The selected alkyl, cycloalkyl, aryl and heteroaryls may be optionally substituted, and $R_5$, $R_6$ are independently selected from the group consisting of H, alkyl, cycloalkyl, aryl, and heteroaryl. Further, $R_5$ and $R_6$ may be optionally substituted.

The L-VS conjugate may subsequently radiolabelled to yield a composition having the general formula:

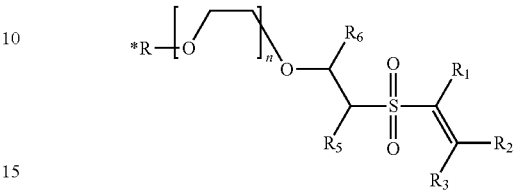

Wherein *R is a radioisotope,
n is between 1 and 20, inclusive, preferably between 1 and 10, inclusive and more preferably between 1 and 5, inclusive $R_1$, $R_2$, and $R_3$ are independently selected from the group consisting of H, alkyl, cycloalkyl, aryl, and heteroaryl. Further, $R_1$ and $R_3$ may be optionally substituted so as to form a $C_3$-$C_8$ cyclic unsaturated ring, and the selected alkyl, cycloalkyl, aryl and heteroaryls may be optionally substituted, and and $R_5$, $R_6$ are independently selected from the group consisting of H, alkyl, cycloalkyl, aryl, and heteroaryl. Further, $R_5$ and $R_6$ may be optionally substituted.

In a preferred embodiment, $R_5$ and $R_6$ are hydrogen.
In another preferred embodiment, $R_1$, $R_2$, $R_3$, $R_5$, and $R_6$ are all hydrogen.

More preferably, the L-VS conjugate has the general formula:

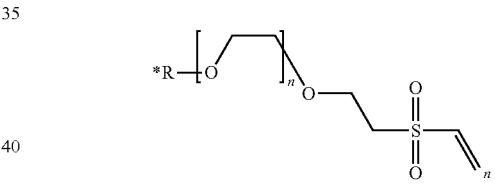

Wherein *R is a radioisotope, and
n is between 1 and 20, inclusive, preferably between 1 and 10, inclusive and more preferably between 1 and 5, inclusive Another aspect of the invention is directed to methods for selectively labeling a biomolecule, A, such as a protein or a polypeptide with a radioactive label, as well the resulting radiolabelled biomolecule. The general structure of the resulting radiolabeled biomolecules can be represented schematically by the general formula:

*R-L-VS-A wherein *R, L, and VS are as defined above and A is selected from the group consisting of a protein, polypeptide, aptamer, DNA oligonucleotide, and other ligands. Suitable proteins, polypeptides, aptamers, DNA oligonucleotides or ligands will generally include or be modified to include at least one cysteine residue or a free thio-reactive functional group capable of reacting with the vinylsulfone group of the label to form a stable attachment. In some embodiment, the attachment is via formation of a covalent thio-ester bond. In other embodiments, attachment may be via non-covalent attachment. Preferably, the biomolecule A, preferably a protein or peptide has between 1 to 10 free thiol-reactive groups and/or cysteine residues. More preferably, the target protein/peptide also has a biological function such as an enzymatic substrate or a structural element involved in certain pathogenic pathways.

In a preferred embodiment, the target protein/peptide is neurotensin or a variant thereof, or a thiolated neurotensin variant, other stabilized neurotensin, multimeric neurotensin, heteromeric neurotensin with other ligands. Neurotensin is a 13 amino acid neuropeptide. Human neurotensin has the amino acid sequence QLYENKPRRPYIL. It has been found that G-protein coupled receptors recognize the same C-terminal recognize the 8-13 hexapeptide sequence Arg(8)-Arg(9)-Pro(10)-Tyr(11)-ILE-(12)-Leu(13). The neurotensin variants of the present invention generally include this 8-13 hexapeptide sequence or variants thereof that include a cysteine residue or thiol group or are modified to include a cysteine/thiol residue. One preferred neurotensin analog is Cys-pipGly-Pro-pipAmGly-Arg-Pro-Tyr-tBuGly-Leu-OH. The exact sequence of the neurotensin analog is not particularly limited so long as it maintains sufficient neurotensin activity contains and contains or is modified to contain at least one cysteine residue or other thiol containing group. Preferably, the neurotensin analog is at least 50% homologous to the 8-13 hexapeptide sequence Arg(8)-Arg(9)-Pro(10)-Tyr(11)-ILE-(12)-Leu(13), excluding any added cysteine residue.

In a preferred embodiment, *R-PEG-VS-A compound has a structure having the formula:

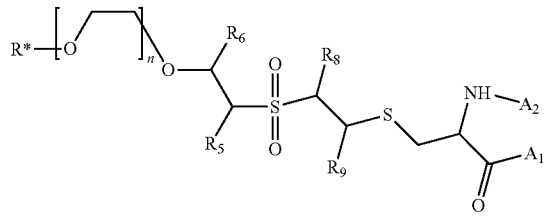

Wherein *R is a radionuclide,
$R_5$, $R_6$, $R_8$, $R_9$ may be independently selected from the group consisting of H, alkyl, cycloalkyl halogen and aryl, each of which may be optionally substituted,
A1 is selected from the group consisting of a protein, polypeptide, aptamer, DNA oligonucleotide, and a ligand;
$A_2$ is selected from the group consisting of H, a protein, peptide, aptamer, DNA oligonucleotide, and a ligand, and wherein, taken together, $A_1$ and $A_2$ may optionally form a polypeptide or cyclic polypeptide.

In a preferred embodiment, the labeling radioactive isotope, *R is $^{18}F$, $R_5$, $R_6$, $R_8$, and $R_9$ are all hydrogen, and $A_2$ and $A_1$ taken together are a neurotensin or a neurotensin variant.

Even more preferably, the radioactive labeling agent is $^{18}F$-DEG-VS and the targeted peptide is neurotensin (i.e. $^{18}F$-DEG-VS-Nr. Such radio-labeled proteins or peptides may be useful as tracers in imaging techniques such as positron emission tomography (PET).

Methods in accordance with this aspect of the invention will generally include the steps of attaching a target protein or peptide with a vinylsulfone radioactive labeling agent as described above. In some embodiments, a step of providing or synthesizing the radioactive labeling agent may be performed shortly before the attaching step. Those skilled in the art will readily recognized that the time period before the providing or synthesizing step may be limited by the half-life of the particular *R label used. With radioactive labels having shorter useful half-lives, the time lag between synthesis and attachment of the *R-VS labeling agent to the target protein/peptide and their ultimate use may be short. In such instances, attachment of the radioactive group must occur within a short period prior to use of the labeled protein/peptide, requiring an on-site system of performing the labeling method. In other instances where the half-life of the *R label is long, labeling of the target protein/peptide may be performed off-site in a mass-production setting, and the resulting labeled protein/peptide be delivered in a packaged format.

Still another aspect of the invention is directed to methods of performing PET imaging utilizing novel tracers of the present invention as described above.

Methods in accordance with this aspect of the invention will generally include the steps of administering to a subject an effective amount of a $^{18}F$-VS labeled tracer compound; and imaging the subject with a PET imaging instrument at locations of interest.

Methods for administering the tracer compound is generally known in the art, which may include, but not limited to intravenous injection, oral administration, or any other modes of administration known in the art.

$^{18}F$ vinylsulfone has at least the following advantages over 18F labeled maleimide: 1) One-step $^{18}F$-fluorination precursor to achieve $^{18}F$ vinylsulfone; 2) The product of the reaction of a thiol with a vinylsulfone gives a single stereoisomer structure, unlike conjugation with maleimides, which produces two potential stereoisomers; and 3) these vinylsulfone groups are stable in aqueous solution for extended periods, as they are not subject to hydrolysis at neutral pH (15). Thus, they retain excellent coupling potential for thiol-containing proteins or other molecules even when used in aqueous buffer conditions.

Figure 7:
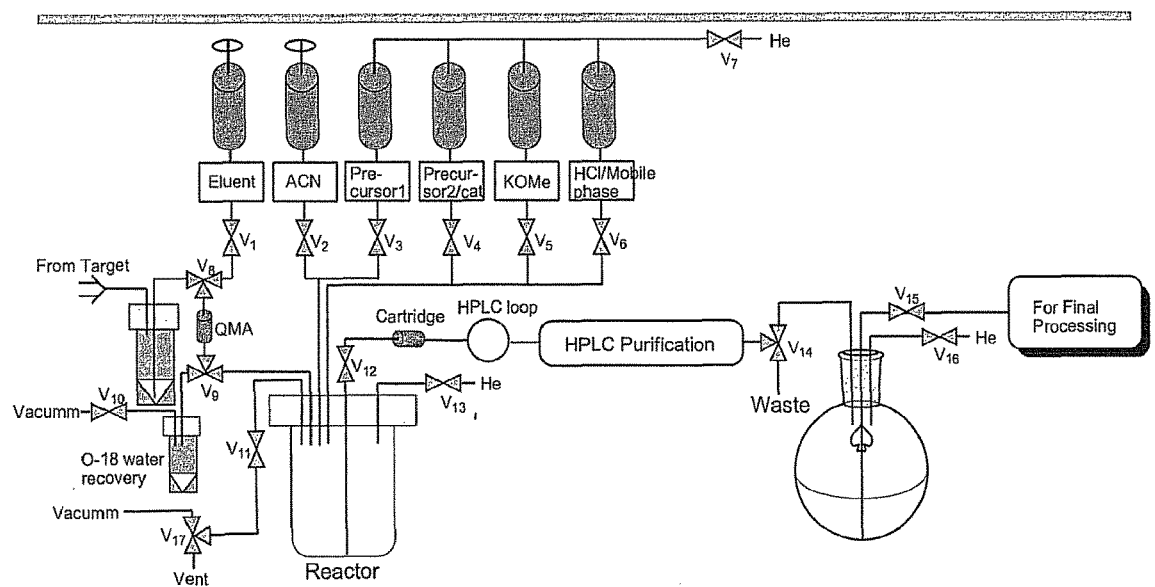
FIG. 7 shows an exemplary schematics of the system/apparatus in accordance with this aspect of the invention.
Figure 8:
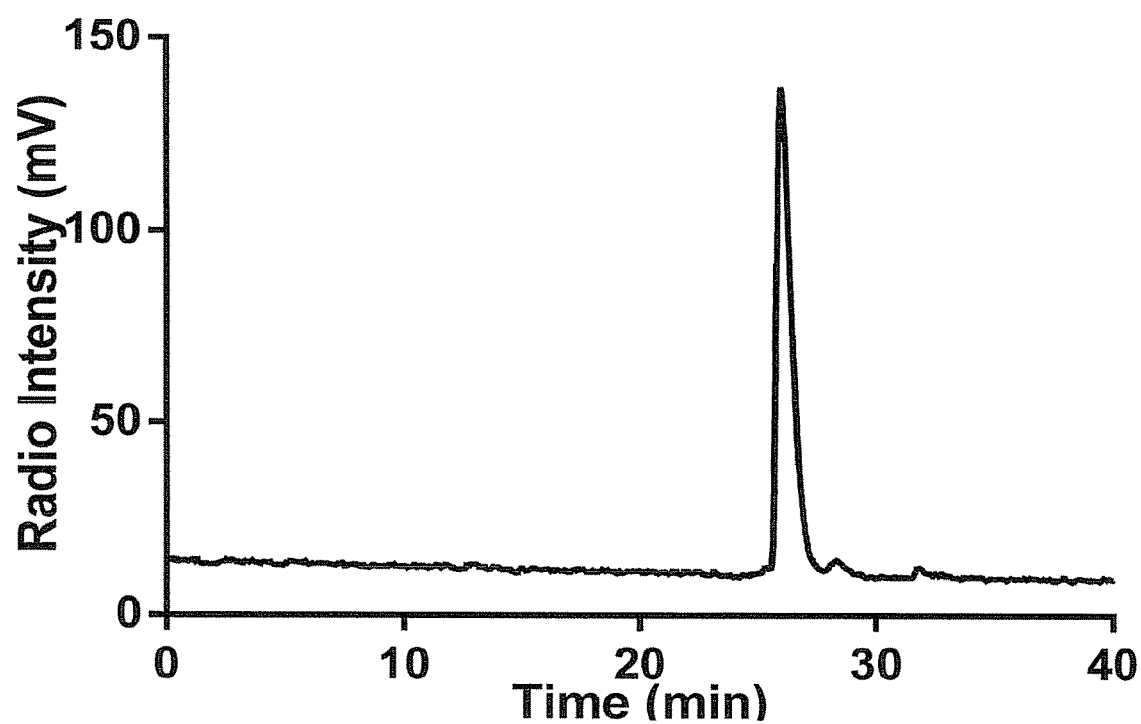
FIG. 8. Radio HPLC trace of $^{18}F$-DEG-VS-NT after 5 hr incubation in 1×PBS at 37° C.
Figure 9:
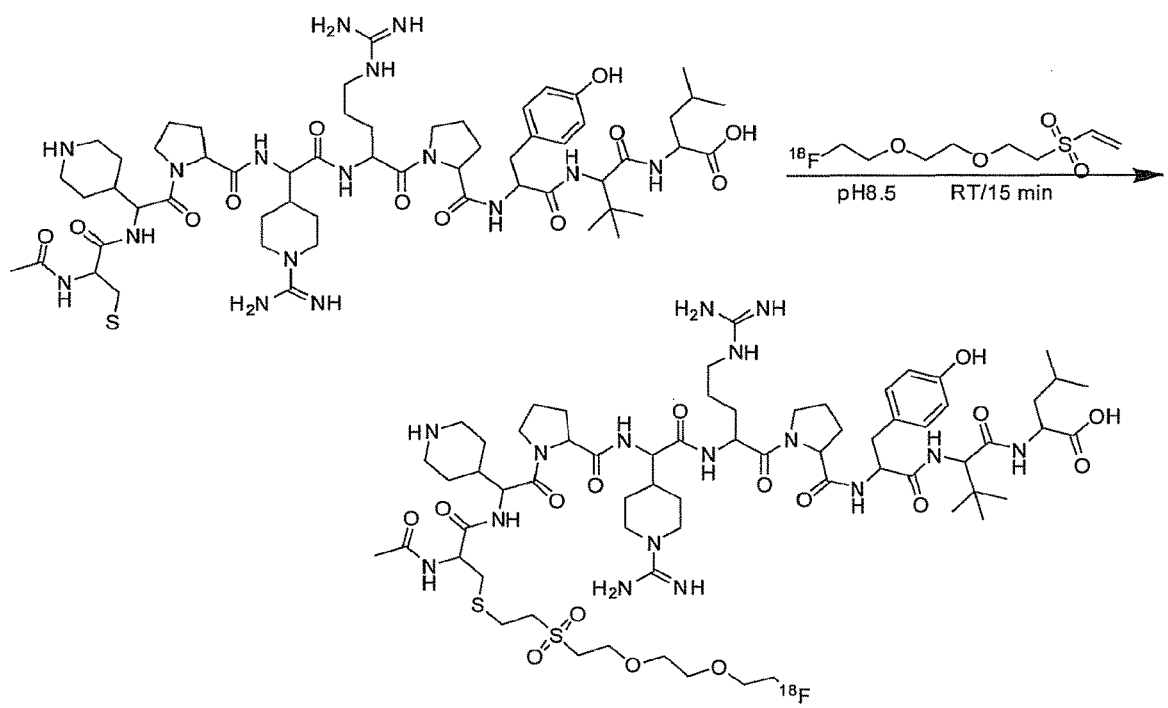
FIG. 9. Radiosynthesis scheme of $^{18}F$-DEG-VS-(Ac)-NT and the corresponding radio-HPLC trace.
Figure 9:
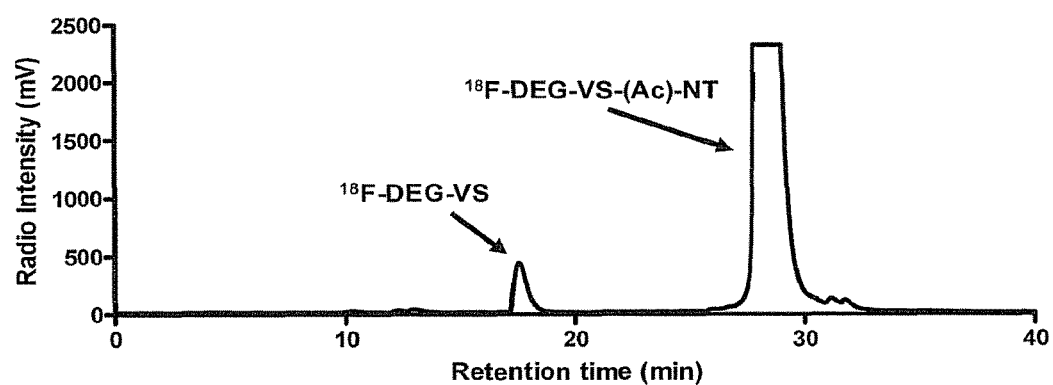

A further aspect of the invention is directed to systems and apparatuses for imaging biological or physiological processes by utilizing the radioactive tracers described above. FIG. 7 shows an exemplary schematics of the system/apparatus in accordance with this aspect of the invention. Embodiments in accordance with this aspect of the invention may include traditional automated or semi-automated box, microwave reactor, or microfluidic reactor, or equivalents thereof.

Brief Description of Certain Results
Chemical Synthesis

As shown in FIG. 1, the F-DEG-VS precursor [2-(2-(2-(vinylsulfonyfletoxy)ethoxy)ethyl 4-nitrobenzenesulfonate (2)] was synthesized with >95% yield and was $^{19}F$-fluorinated by reaction with TBAF. $^{19}F$-DEG-VS was used as a chemical standard for the reaction conditions and HPLC location of $^{18}F$-DEG-VS conjugates.

Figure 2A:
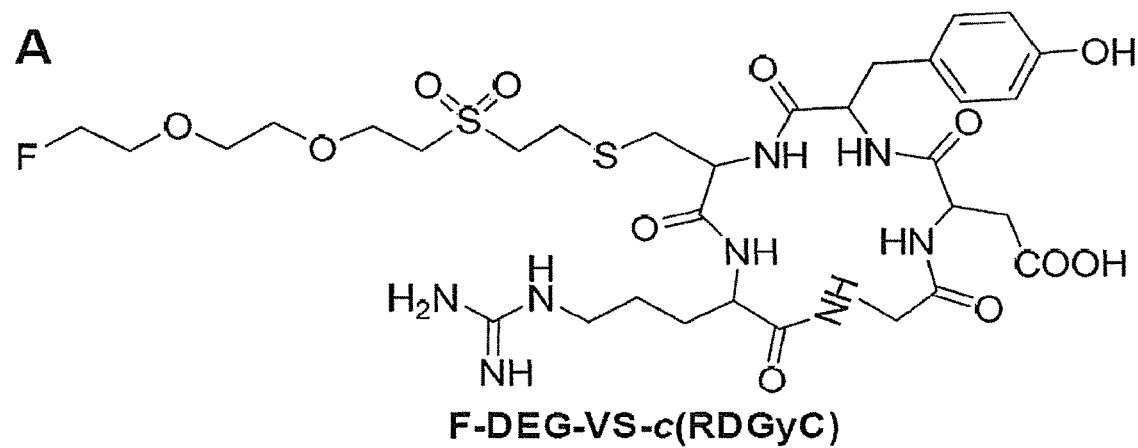
FIG. 2. (A) Chemical structure of F-DEG-VS-c(RGDyC) and F-DEG-VS-c(RGDyK); (B) HPLC profile of the crude reaction of $^{19}F$-DEG-VS-c(RGDyC), $^{19}F$-DEG-VS-c(RGDyK), $^{18}F$-DEG-VS with c(RGDyC)/c(RGDyK) (radio), and the standard of $^{19}F$-DEG-VS-c(RGDyC) on radio-HPLC (UV).
Figure 2A:
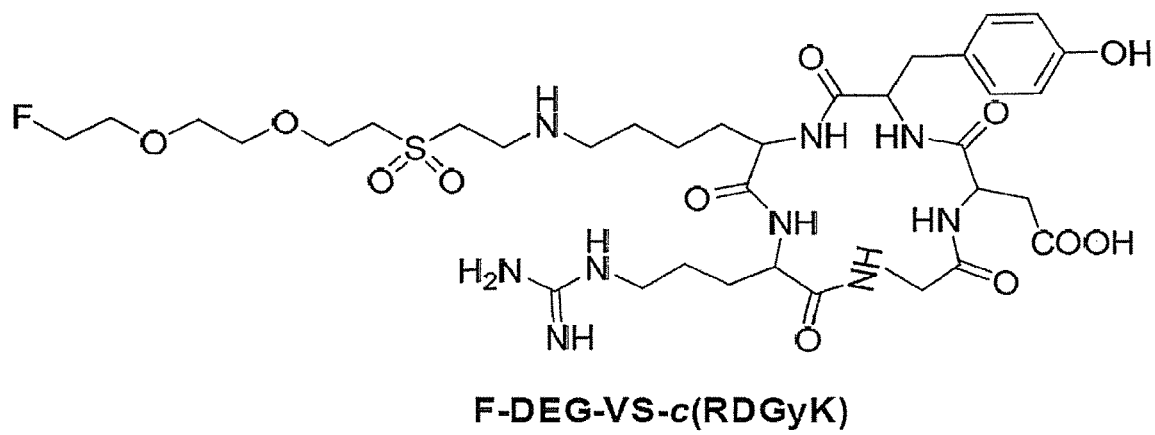
Figure 2B:
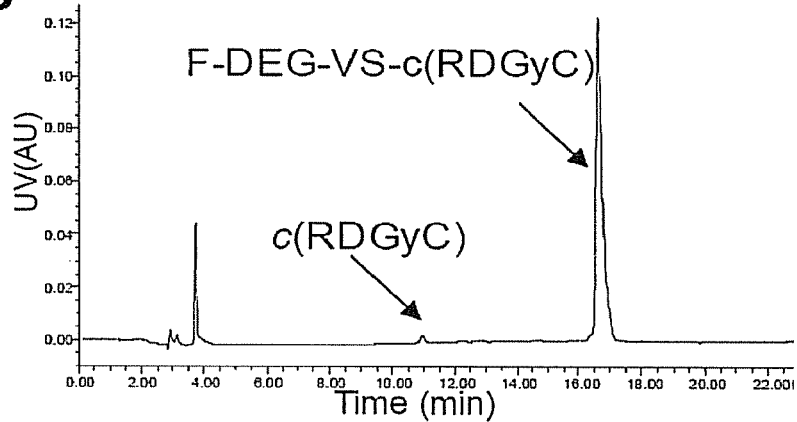
Figure 2B:
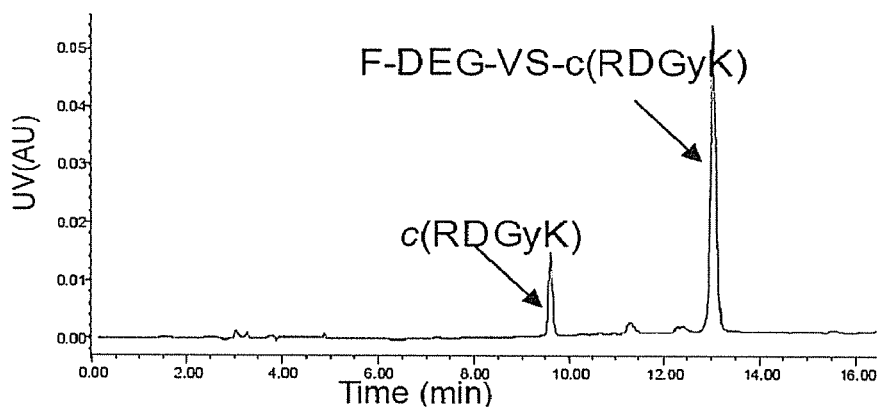
Figure 2B:
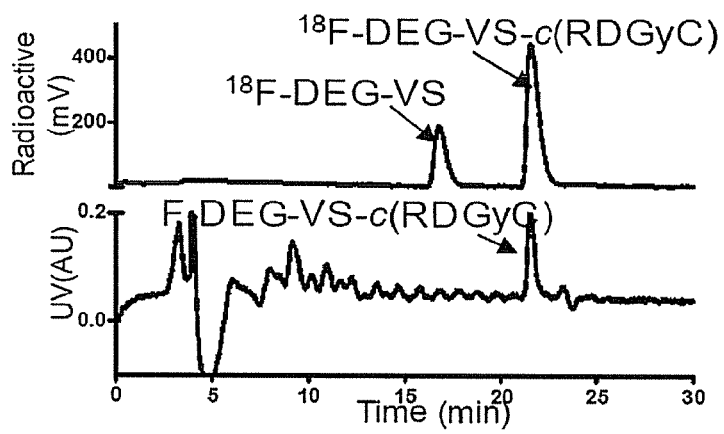

We first evaluated the cold reaction between $^{19}F$-DEG-VS and cRGDyC (with a free SH group) and cRGDyK (with a free —$NH_2$ group) peptides (see FIG. 2A). Both cRGDyC and cRGDyK reacted with $^{19}F$-DEG-VS, however, cRGDyK reacted only at pH higher than 8.5 after overnight incubation, compared with pH 7.0 and 30 min incubation for cRGDyC (FIG. 2B).

Figure 3A:
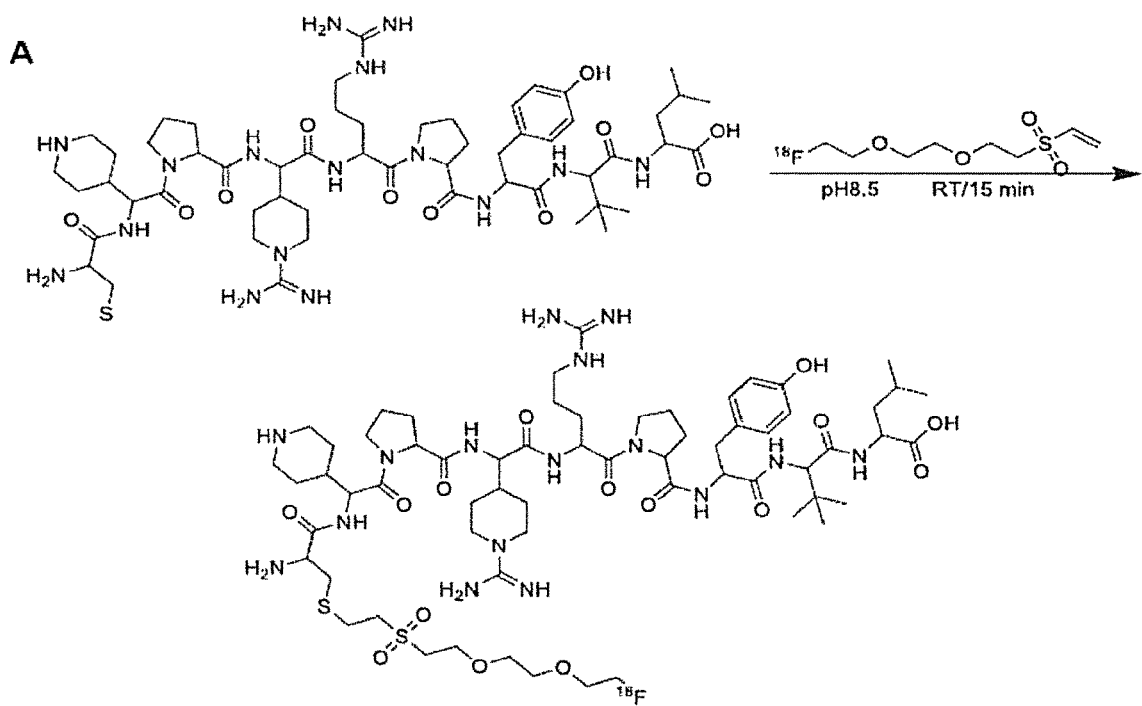
FIG. 3 shows exemplary radiosynthesis scheme in accordance with embodiments of the present invention. (A) Radiosynthesis scheme of $^{18}F$-DEG-VS-NT. (B) HPLC profile of the crude reaction of $^{19}F$-DEG-VS and NT; (C) HPLC profiles of t $^{18}F$-DEG-VS-NT (Radioactive) $^{19}F$-DEG-VS-NT (UV), and ($^{19}F$-DEG-VS)$_2$-NT (UV).
Figure 3B:
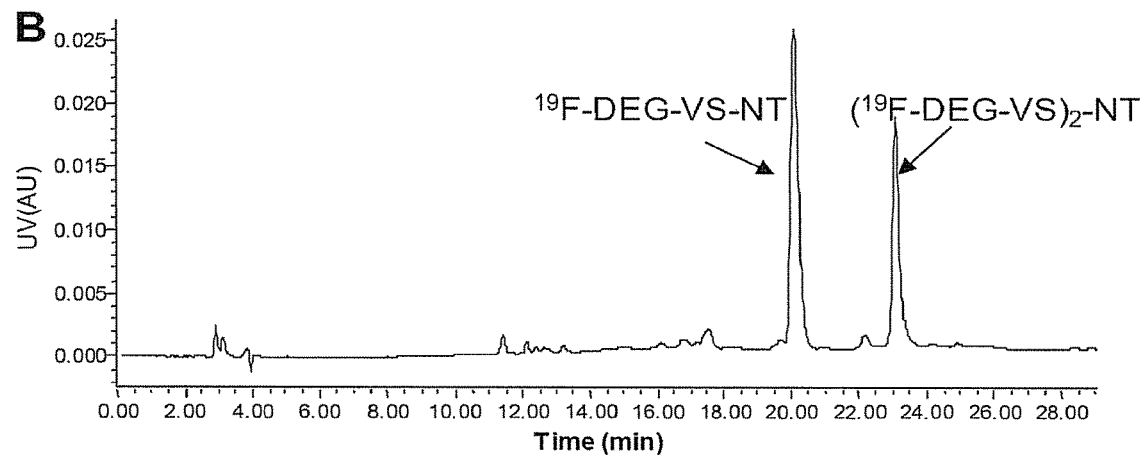

Thiolated NT also reacted with $^{19}F$-DEG-VS efficiently. However, two products [$^{19}F$-DEG-VS-NT and ($^{19}F$-DEG-VS)$_2$-NT] (FIGS. 3A and 3B) were obtained when the reaction was performed at high pH (eg., pH 9.0), due to its reaction with one thiol and one amine group present in our NT analogue. Radiochemistry The $^{18}F$ labeling of the VS-synthon was tested at various solvent, concentration and temperature conditions. Representative results are shown in Table 1. At 10 mg precursor loading, the radiolabeling yield for $^{18}$F-DEG-VS was calculated to be 90% yield based on HPLC integration. A further increase in the precursor loading only marginally increased the yield to 95% (see Table 1). A representative radio-HPLC trace of the crude labeling reaction is shown in FIG. 1B. $^{18}$F-DEG-VS demonstrated good in vitro stability and the radiochemical purity was still more than 99% at 4 hr post HPLC purification after incubation in PBS (FIG. 2C).

For the $^{18}$F-reaction, we incubated equal molar amounts of cRGDyC and cRGDyK with $^{18}$F-DEG-VS in the same reactor. In this case, we only observed the product from cRGDyC and $^{18}$F-DEG-VS (FIG. 2B). The absence of product from cRGDyK/$^{18}$F-DEG-VS demonstrated the selectivity of this reaction for the thiol over the amino group. Thus even at high pH, $^{18}$F-DEG-VS selectively labeled the thiol group in the presence of a free amino group.

Figure 3C:
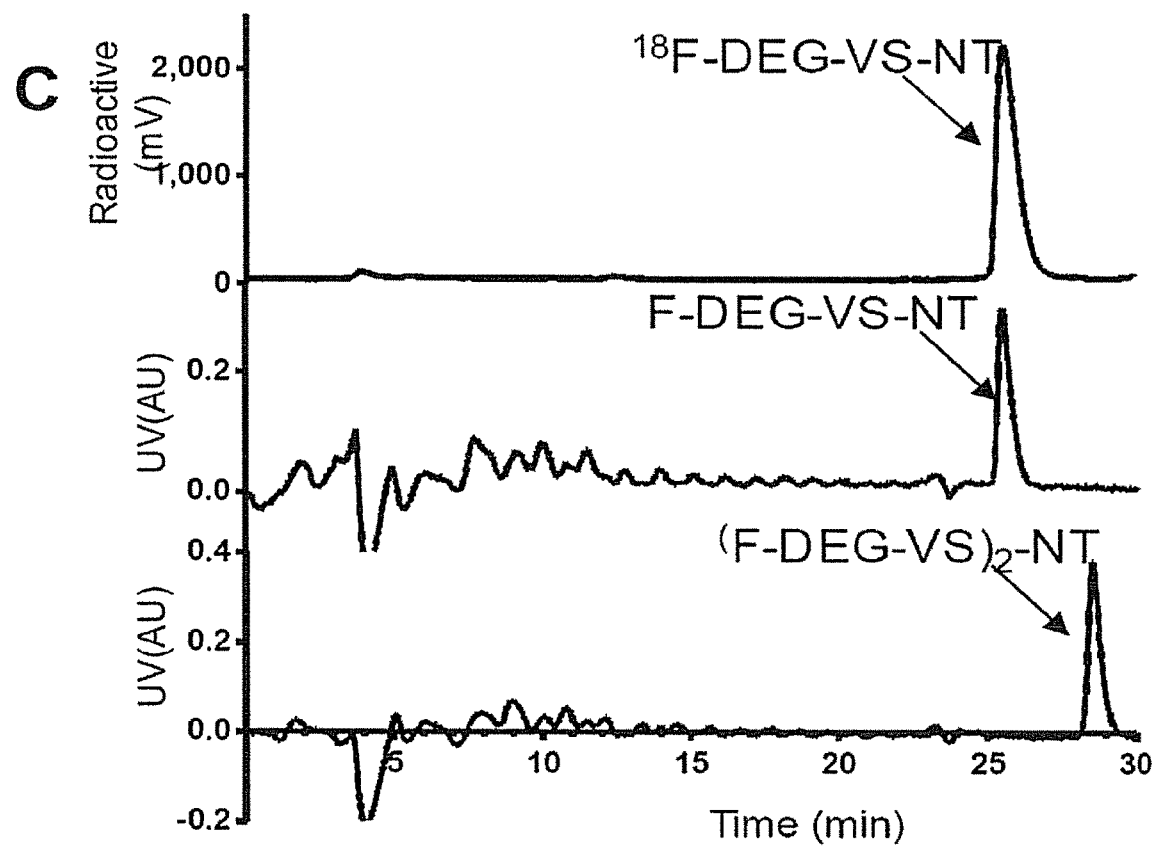
Figure 11:
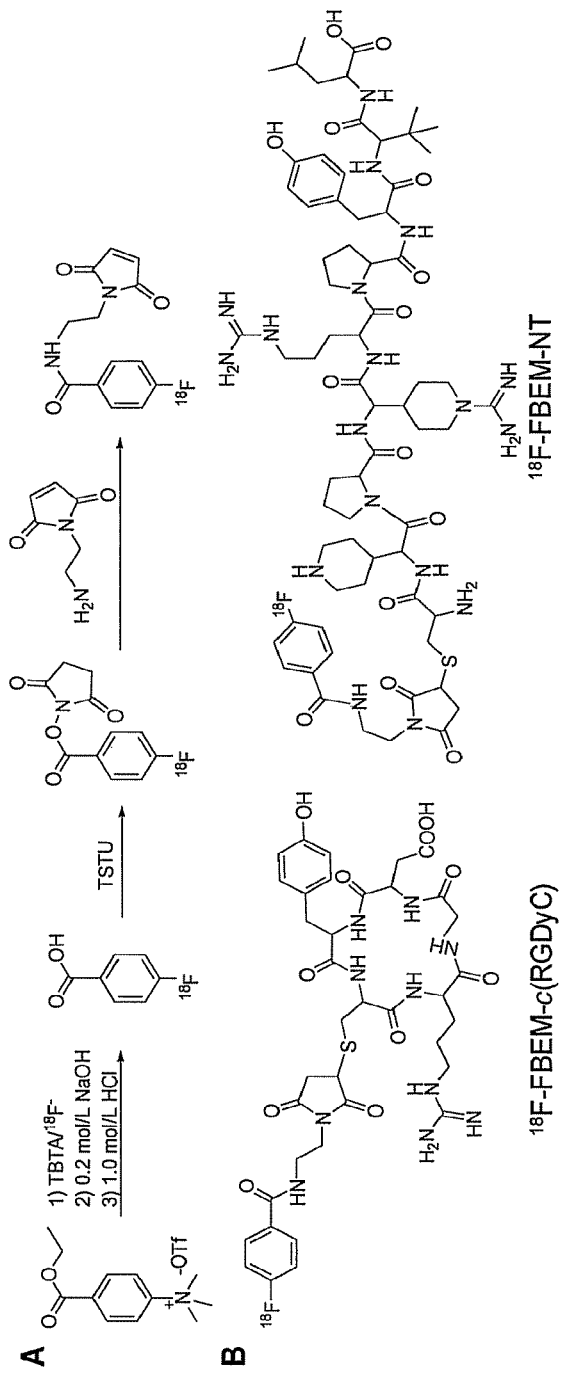
FIG. 11. (A) Radiosynthesis scheme of $^{18}F$-FBEM; (B) Chemical structure of $^{18}F$-FBEM-c(RGDyC) and $^{18}F$-FBEM-NT.

$^{18}$F-DEG-VS also efficiently reacted with thiolated NT. The (F-DEG-VS)$_2$-NT byproduct seen with the $^{19}$F-synthesis was not observed in radiolabeling reaction as shown by HLPC (FIG. 3C). The radiochemical purity of 18F-DEG-VS-NT was still greater than 95% at 5 hrs post HPLC purification after incubation in PBS. In order to compare 18F-DEG-VS with a thiol specific maleimide based reagent, 18F-FBEM was also prepared and shown to react efficiently with c(RGDyC) and thiolated NT, respectively (FIG. 11).

In Vitro Cell Binding Affinity

Figure 4:
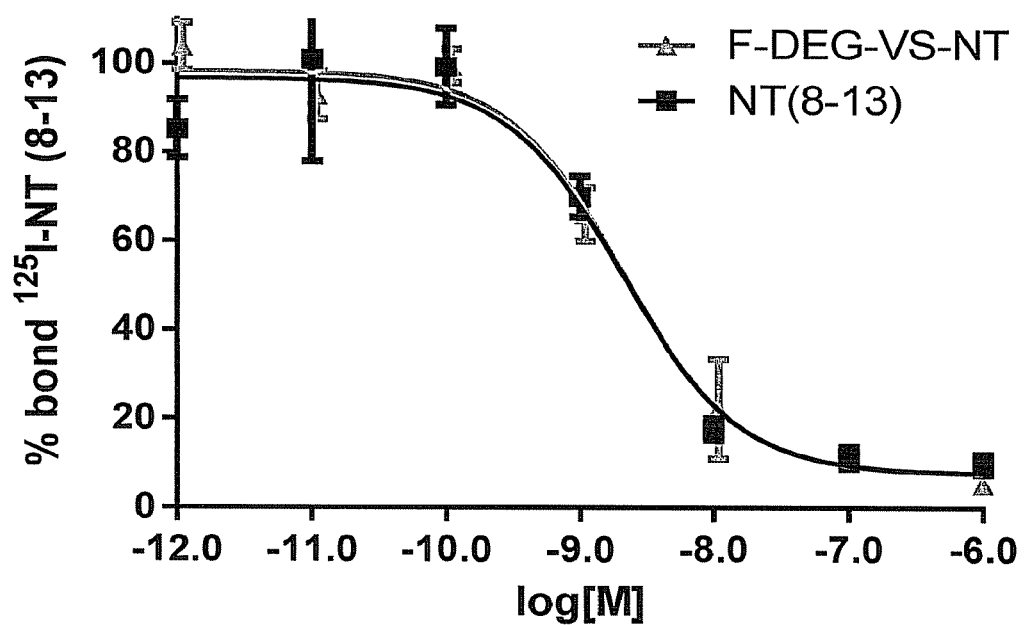
FIG. 4 shows exemplary results of competitive binding assays in accordance with embodiments of the present invention. Competitive binding assays of $^{125}I$-NT(8-13) and $^{19}F$-DEG-VS-NT or NT(8-13) in HT-29 cells. Data are mean±SE (n=3). X axis reflects concentration of non-radiolabeled competitor. IC$_{50}$ values for $^{19}F$-DEG-VS-NT and NT(8-13) were 2.03±0.22 and 2.12±0.26 nmol/L, respectively.

We compared the receptor-binding affinity of $^{19}$F-DEG-VS-NT with that of NT (8-13) using a competitive cell-binding assay (FIG. 4). Both peptides inhibited the binding of $^{125}$I-NT (8-13) to NTR1 positive HT-29 cells in a dose-dependent manner. The IC$_{50}$ value for $^{19}$F-DEG-VS-NT (2.03±0.22 nmol/L) was comparable to that of NT (8-13) (2.12±0.26 nmol/L).

The results clearly demonstrated that F-DEG-VS-NT has similar in vitro receptor-binding affinity to NTR1 as NT (8-13).

Biodistribution and microPET Imaging

Figure 5:
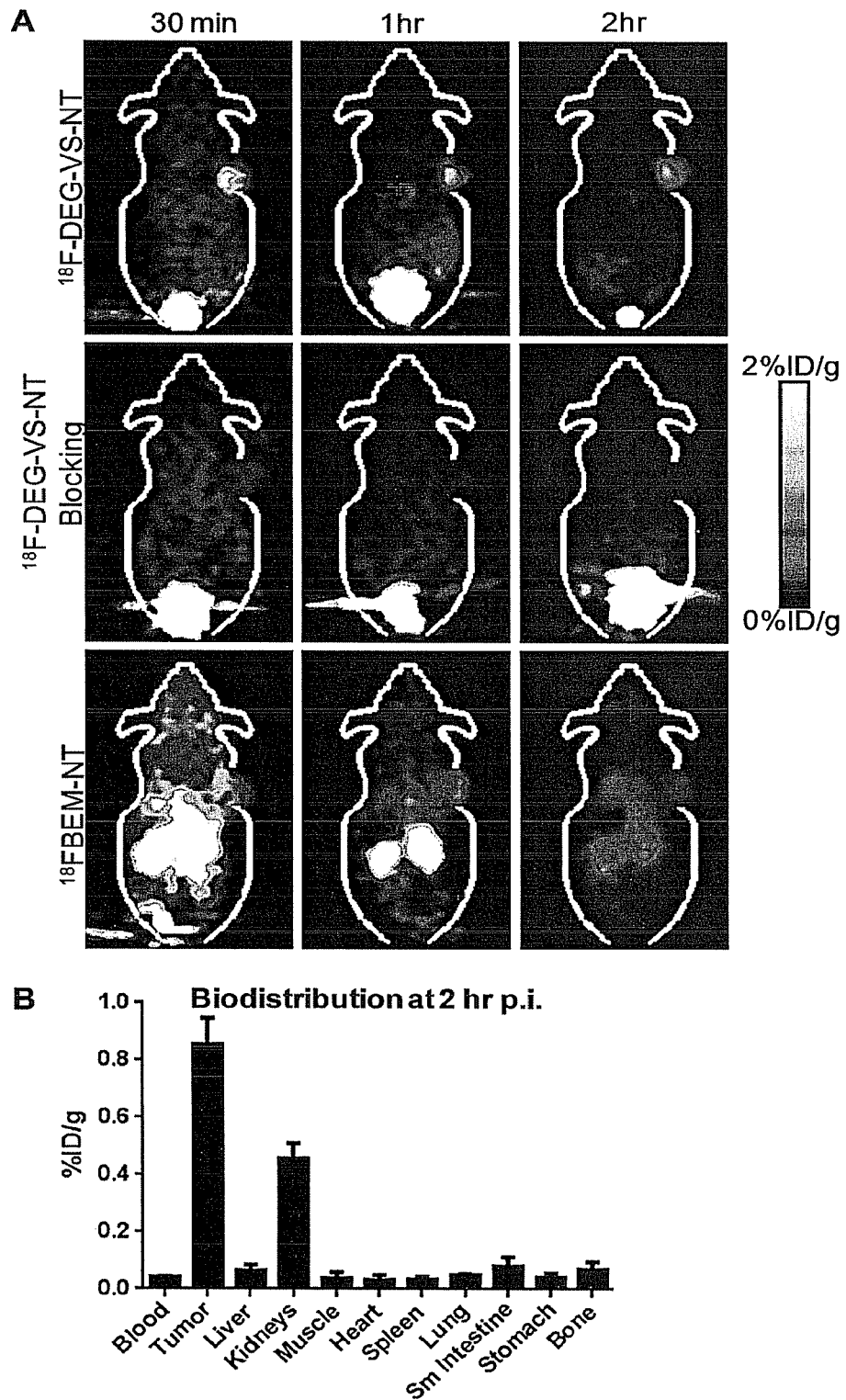
FIG. 5. (A) Representative coronal microPET images of mice bearing HT-29 xenografts after injection of 3.7 MBq $^{18}F$-DEG-VS-NT without (upper) and with unradiolabeled NT(8-13) (middle), and 3.7 MBq $^{18}F$-FBEM-NT (lower); (B) The biodistribution of $^{18}F$-DEG-VS-NT in mice bearing HT-29 xenograft at 2 hr p.i.
Figure 13:
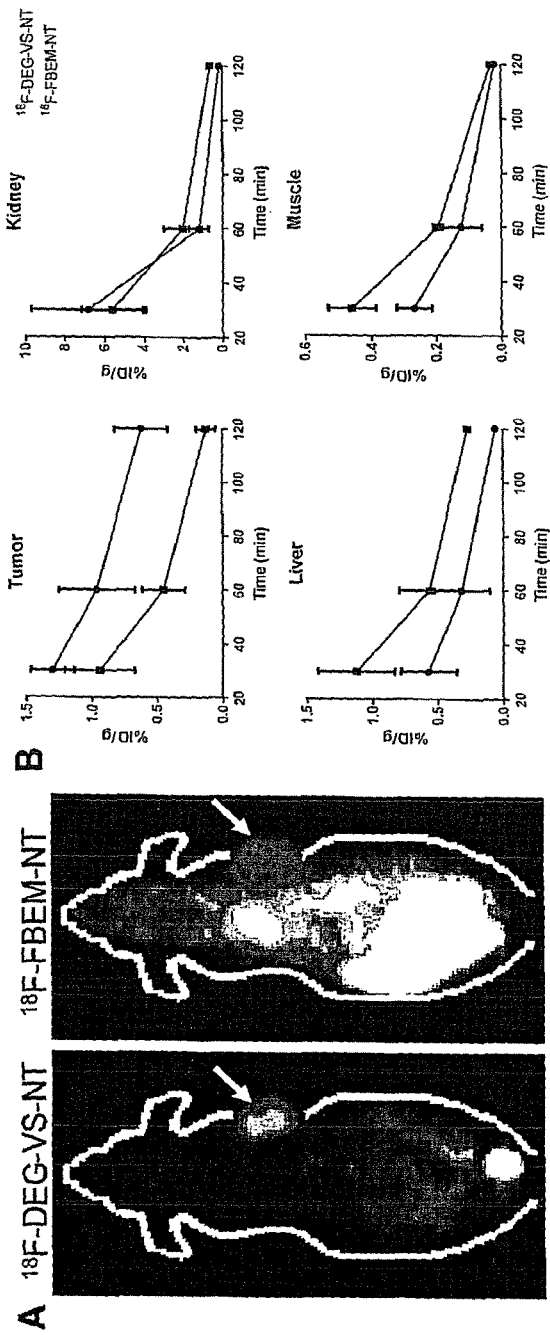
FIG. 13. (A) 2-D projection microPET images of mice bearing HT-29 tumor at 2 hr after injection of $^{18}F$-DEG-VS-NT and $^{18}F$FBEM-NT (arrows indicate HT29 tumors); (B) Time activity curves of tumor, kidney, liver, and muscle after injection of $^{18}F$-DEG-VS-NT and $^{18}F$FBEM-NT.

The neurotensin receptor 1 (NTR1) targeting efficacy of $^{18}$F-DEG-VS-NT was evaluated in HT-29 xenografts (NTR1 positive) at multiple time points (0.5, 1, and 2 hr p.i.) with microPET. As shown in FIG. 5A. The HT-29 tumors were clearly visualized with high tumor-to-background contrast for $^{18}$F-DEG-VS-NT and the tumor uptake was 1.30±0.17, 0.96±0.29, and 0.63±0.20% ID/g at 0.5, 1, and 2 hr p.i., respectively. In comparison, $^{18}$F-FBEM-NT also demonstrated prominent uptake in tumor (0.13±0.08% ID/g), but was significantly (p=0.017) lower than observed for $^{18}$F-DEG-VS-NT at 2 hr p.i. The liver and kidney uptake of $^{18}$F-FBEM-NT was 0.28±0.03% ID/g and 0.64±0.02% ID/g at 2 hr p.i. respectively. Compared with $^{18}$F-FBEM-NT, $^{18}$F-DEG-VS-NT exhibited superior tumor-to-background contrast and lower abdomen background (FIG. 13).

The NTR1 specificity of $^{18}$F-DEG-VS-NT was confirmed by a blocking experiment where the radio-tracer was co-injected with an excess of unlabeled NT(8-13). As can be seen from FIG. 5A, in the presence of unlabeled NT(8-13), the NTR1 tumor uptake (0.47, 0.15, and 0.04% ID/g at 0.5, 1, and 2 hr p.i., respectively) was significantly (p<0.01) lower than that without NT(8-13) blocking at all time points. The kidney uptake rapidly decreased from 6.82±2.90% ID/g at 0.5 hr p.i. to 0.17±0.01% ID/g at 2 hr p.i. Based on imaging analysis, tumor-to-kidney ratio, tumor-to-liver ratio, and tumor-to-muscle ratio was 3.69±1.50, 10.33±4.01, and 27.12±5.46 at 2 hr p.i. respectively. At 2 hr p.i., tumor demonstrated significantly higher uptake than those in kidney, liver and muscle. Other organs, including heart and lung, were essentially at background levels by 2 hr p.i.

In addition to the microPET study, we also performed biodistribution studies using a separate group of HT-29 tumor bearing mice at 2 hr p.i. of $^{18}$F-DEG-VS-NT. As shown in FIG. 5B. The tumor and kidney uptake was 0.86±0.09% ID/g and 0.46±0.05% ID/g, respectively. At 2 hr p.i., tumor demonstrated significantly higher uptake than those in kidney, liver and muscle (FIG. 5B). Other organs, including heart, and lung, were essentially at background levels by 2 hr p.i.

Metabolic Stability Study

Figure 6:
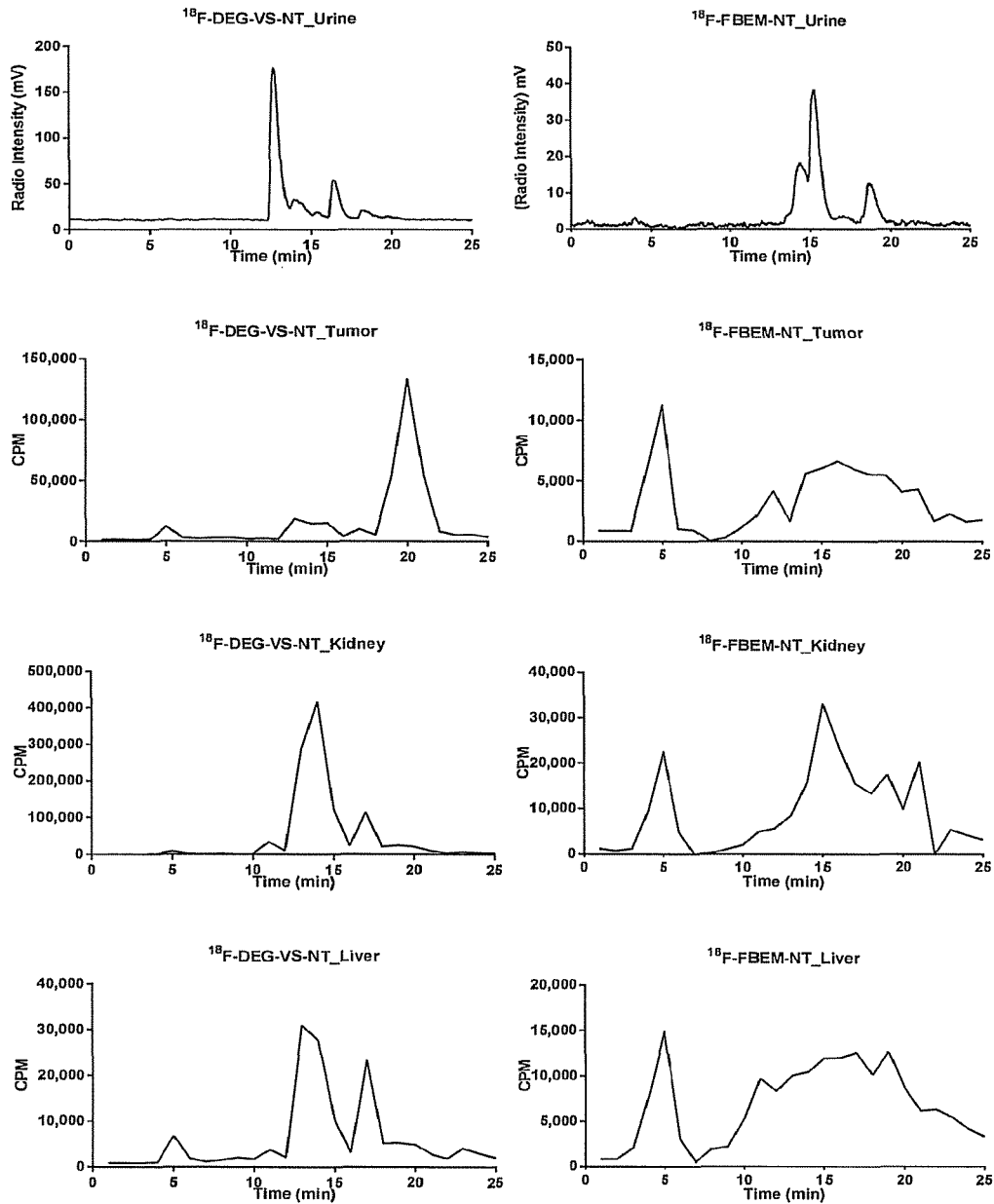
FIG. 6 shows the metabolic stability of $^{18}F$-DEG-VS-NT and $^{18}F$-FBEM-NT in urine, tumor, kidney, and liver. The retention time for $^{18}F$-DEG-VS-NT and $^{18}F$-FBEM-NT was 18.5 min and 19.0 min, respectively.
Figure 10:
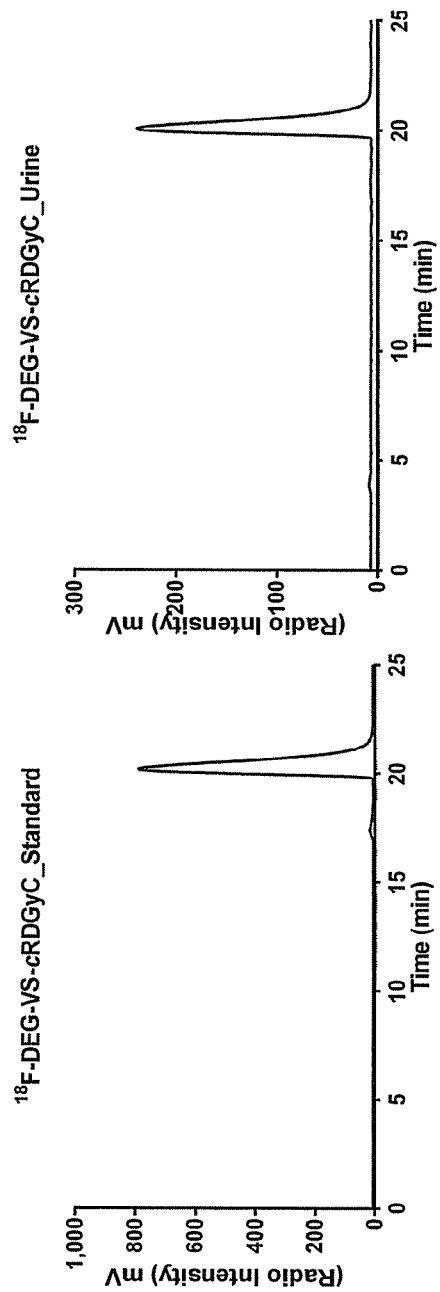
FIG. 10. The radio HPLC profiles of $^{18}F$-DEG-VS-c (RGDyC) standard and the metabolic stability in urine.
Figure 12:
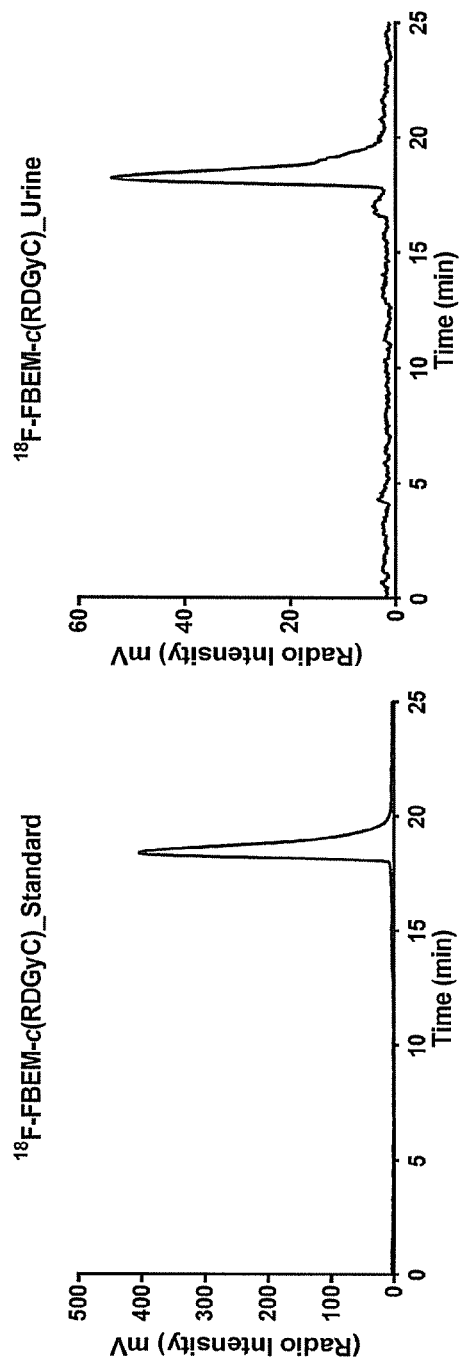
FIG. 12. The radio HPLC profiles of $^{18}F$-FBEM-c (RGDyC) standard and the metabolic stability in urine.

The metabolic stability of $^{18}$F-DEG-VS-NT was determined in mouse urine and in the liver, kidneys, and HT-29 tumor homogenates at 1 hr p.i. The HPLC chromatograms are shown in FIG. 6. The retention time of intact $^{18}$F-DEG-VS-NT was 18.50 min. A major metabolite peak was found at about 20 min for the tumor and two major metabolite peaks were found at 13-15 min and 17 min for urine, kidney and liver samples. No significant defluorination was observed throughout the study. The metabolic stability of $^{18}$F-FBEM-NT was also studied. The retention time of intact $^{18}$F-FBEM-NT was 19.02 min. Besides the multiple peaks between 15-21 min, there was a major peak at about 5 min for tumor, kidney and liver. We also synthesized the $^{18}$F-DEG-VS-c(RGDyC) and $^{18}$F-FBEM-c(RGDyC), and analyzed their urine metabolites. Unlike the unstable NT peptide, the c(RGDyC) is stable in vivo. Accordingly, $^{18}$F-DEG-VS-c(RGDyC) gave a single peak corresponding to intact labeled peptide excreted in urine (FIG. 10). $^{18}$F-FBEM-c(RGDyC) also gave a major peak, plus additional peaks (FIG. 12).

Brief Discussion of Certain Aspects of the Invention

Accumulating evidence suggests that neurotensin receptors play key roles in cancer growth and survival (16, 19). In fact, NTRs have been proposed as a promising marker for human pancreatic carcinoma, breast cancer, head and neck carcinoma, prostate and non-small cell lung cancer (19-28).

The development of imaging agents to obtain NTR expression profiles or "fingerprints" of individual tumors could therefore lead to efficient early stage diagnosis and customized treatment options for cancer patients. Neurotensin, a tridecapeptide ligand for NTR, is metabolized rapidly in plasma by endogenous peptidases. In order to improve the in vivo stability, various NT analogues have been developed. For example, a number of radiolabeled neurotensin analogues were recently developed as a valuable tool for both imaging and therapy of neurotensin receptor-positive tumors (29-35). Although encouraging results have been obtained in these initial studies, the relatively high kidney uptake and suboptimal tumor to tissue contrast warrant further improvement of these agents, especially in the choice of the radiolabel. Previously, we have demonstrated that the pharmacokinetics of peptide based PET probes improved significantly by substituting $^{18}$F in place of $^{64}$Cu (36, 37). In fact, as one of the commonly used PET radioisotopes, $^{18}$F can also be easily produced in high quantities in a medical cyclotron with an ideal half-life of 110 min for imaging applications (1). Therefore, we have devoted a significant amount of effort to develop a $^{18}$F-labeled PET probe for NTR targeted imaging.

Since cysteines are much less abundant than lysines, aspartic acid, and glutamic acid residues in peptides and proteins, thiol-reactive agents have been used to site-selectively modify these biomolecules. Previously, several thiol-reactive $^{18}$F-synthons have been reported, most of which bear a maleimide group for conjugate addition of thiols under mild conditions. However, most thiol reactive synthons require multistep reactions, which could be time consuming and labor intensive.

In recognition of the above issues, we sat out to develop a platform technology based on the Michael addition reactivity of vinyl sulfone. Vinyl sulfone chemistry has been demonstrated to be suitable for the selective modification of cysteine residues under mild conditions (15). The water stability of the vinyl sulfone function, the lack of by-products, the almost quantitative yields of the reaction with thiols, and the chemical stability of the thioether linkage formed make this reaction an appealing approach for $^{18}$F labeling.

Our VS based prosthetic group was designed to be hydrophilic, a highly desirable attribute for in vivo applications. In order to simply the labeling procedures, initial efforts were focused on a one-step radiofluorination of VS. Radiofluorination reactions were carried out in MeCN/DMSO using azeotropically dried [$^{18}$F]-TBAF. Conversion of VS-synthon to the corresponding [H]-DEG-VS was found to be strongly dependent on the VS-synthon reaction concentration and temperature. Under optimized conditions, >90% labeling yield could be obtained within 15 min. The isolated yield was determined to be 35±6%.

Since VS may also react with primary amines at high pH (15), we decided to explore the selectivity of the VS-synthon reaction under mild conditions. Although both cRGDyK and cRGDyC efficiently react with $^{19}$F-DEG-VS reagent, cRGDyK is much less reactive, which required overnight incubation and higher pH compared with 30 min incubation for cRGDyC. However, using the $^{18}$F-DEG-VS reagent, only cRGDyC reacted in the equi-molar mixture of cRGDyK and cRGDyC. This result clearly demonstrated the chemoselectivity of $^{18}$F-DEG-VS towards SH functional group.

After establishing the efficient $^{18}$F-DEG-VS labeling method, $^{18}$F labeling of thiolated neurotensin peptide was performed. $^{18}$F-DEG-VS-NT was obtained in >95% yield within 35 min and the radiochemical purity was more than 99%. The specific radioactivity of $^{18}$F-DEG-VS-NT was determined based on a literature method (38) in which the UV integration of final product was compared with a standard titration curve, yielding a specific radioactivity of 19.2±4.3 TBq/mmol for $^{18}$F-DEG-VS-NT.

Since the chemical modification of a peptide can significantly decrease receptor binding affinity, an in vitro cell binding assay of $^{19}$F-DEG-VS-NT and unmodified NT was performed. The affinity decrease induced by VS-synthon conjugation was negligible, as supported by the similar IC$_{50}$ of $^{19}$F-DEG-VS-NT and unmodified NT (8-13). The imaging quality of $^{18}$F-DEG-VS-NT was evaluated in vivo using an HT-29 xenograft model, which has been well established to have high NTR1 expression (16). $^{18}$F-DEG-VS-NT had a rapid renal clearance. $^{18}$F-DEG-VS-NT predominantly accumulated in the kidneys (6.82±2.90% ID/g) at 30 min p.i. and quickly decreased to 1.19±0.49% ID/g at 1 h p.i. and 0.17±0.01% ID/g at 2 h p.i. Since the activity decreased rapidly in all major organs, a high tumor to organ ratio was obtained at 2 h p.i. including tumor/muscle (27.12±4.56), tumor/liver (10.33±4.01) and tumor/kidneys (3.69±1.50). In the blocking experiment, non-radioactive NT peptide significantly (p<0.01) inhibited the tumor uptake of $^{18}$F-DEG-VS-NT (FIG. 5A) at all time-points, which clearly demonstrated the receptor specificity of this imaging agent. As the tracer has very low uptake in the abdominal region, we also performed a biodistribution study to determine the uptake in liver, kidney, small intestine, spleen, stomach, and other organs or tissues more accurately. As shown in FIG. 5B, the uptakes in these organs were close to background level, which correlates well with the high contrast tumor image obtained from the microPET scan. Since the activity decreased rapidly in all major organs, a high tumor to organ ratio was obtained at 2 hr p.i. including tumor/muscle (30.65±22.31), tumor/liver (11.86±1.98) and tumor/kidneys (1.91±0.43), calculated by biodistribution study. As NT peptide has two potential reactive sites, (Ac)-NT was also synthesized, which could also be efficiently labeled with $^{18}$F-DEG-VS. It still needs to be determined whether this new agent will have similar tumor targeting capability as $^{18}$F-DEG-VS-NT.

While on aspect of the present invention is the development of new thiol-specific, $^{18}$F-radiolabeling methods and composition for peptides and its evaluation by PET imaging, a direct in vivo comparison with an existing maleimide based reagent was made in order to demonstrate the potential advantages of the newly developed labeling strategy. Therefore, a maleimide based reagent, namely $^{18}$F-FBEM-NT, was also synthesized for a direct comparison of imaging quality and metabolic stability. As shown in FIG. 12, $^{18}$F-FBEM-NT was a more complicated synthesis involving 5 steps: fluorination, hydrolysis, activation of the carboxyl group, reaction with the maleimide derivative, and conjugation with Cys-NT. In comparison, the synthesis of $^{18}$F-DEG-VS-NT involves only two steps: fluorination of the synthon and conjugation to Cys-NT. Importantly on PET imaging, 18F-FBEM-NT demonstrated significantly higher background and lower contrast compared with $^{18}$F-DEG-VS-NT. In order to determine if the lower abdominal background and high tumor uptake observed for $^{18}$F-DEG-VS-NT compared with $^{18}$F-FBEM-NT, were caused by a difference in metabolism, a metabolic stability study was performed. As shown in FIG. 6, both $^{18}$F-DEG-VS-NT and $^{18}$F-FBEM-NT exhibited several metabolites in vivo. However, a major metabolite peak at about 5 min was found for $^{18}$F-FBEM-NT but not for $^{18}$F-DEG-VS-NT. Nonetheless, due to the short half-life of NT in man and rodents (39, 40), a conclusion cannot be drawn based on just the above experiments. In a further approach, we have conjugated the more metabolically stable c(RGDyC) peptide with both synthons and studied the urine metabolism of $^{18}$F-FBEM-c(RGDyC) and $^{18}$F-DEG-VS-c(RGDyC). As shown in FIGS. 10 and 12, $^{18}$F-FBEM-c(RGDyC) has additional metabolites in urine not seen for $^{18}$F-DEG-VS-c(RGDyC). This experiment suggests that our VS-based synthon is more stable in vivo than the maleimide based synthon. Thus, the metabolites observed in $^{18}$F-DEG-VS-NT study may be mainly caused by the degradation of the NT peptide and not the synthon itself. Although maleimide based synthons like $^{18}$F-FBEM are expected to be unstable based on literature reports, they may still perform well within the time scale of an $^{18}$F imaging study. We conclude that the observed superior contrast of $^{18}$F-DEG-VS-NT compared to $^{18}$F-FBEM-NT in an animal model warrants consideration of clinical translation of this agent for NTR targeted imaging in human.

The present invention will now be described in detail by referring to the specific exemplary embodiments as illustrated in the accompanying figures.

Example 1

In this illustrative example, we describe how to make and use one of the specific $^{18}$F-labeling agent disclosed herein, $^{18}$F-DEG-VS. We demonstrate conjugation of the $^{18}$F-DEG-VS to free thiol groups in the bioligand neurotensin (NT).

Since accumulating evidence suggests that neurotensin receptors (NTRs) play key roles in cancer growth and survival (16, 17), we used a thiolated NT peptide to demonstrate the potential of $^{18}$F-DEG-VS as a peptide labeling agent. The resulting $^{18}$F-labeled-NT derivative was further evaluated by PET in rodent model with an NTR1 positive tumor.

1. Material and Methods

General Matters

All commercially available chemical reagents were purchased from Aldrich and used without further purification. cRGDyC and cRGDyK were purchased from Peptides International Inc (Louisville, Ky.). A thiolated neurotensin peptide analogue was synthesized by the City of Hope peptide synthesis core using standard FMOC chemistry. No-carrier-added $^{18}$F-fluoride was produced via the $^{18}$O(p, n)$^{18}$F reaction by the bombardment of an isotopically enriched [$^{18}$O] water target (95% enrichment, Isonics, Golden, Colo.) with 11-MeV protons using a Siemens RDS-112 negative ion cyclotron.

All HPLC conditions are gradient. HPLC Method 1: Phenomenex® C18 column (250×4.6 mm, 5 micron); 1 mL/min flow rate; and eluent gradient: 0-2 min 95% solvent A [0.1% trifluoroacetic acid (TFA) in water] and 5% solvent B [0.1% TFA in acetonitrile (MeCN)]; 2-7 min 95-85% solvent A and 5-15% solvent B; 7-27 min 85-70% solvent A and 15-30% solvent B. HPLC Method 2: Phenomenex® C18 column (250×4.6 mm, 5 micron); 1 mL/min flow rate; and eluent gradient: 0-2 min 95% solvent A and 5% solvent B; 2-22 min 95-5% solvent A and 5-95% solvent B. HPLC Method 3: Phenomenex® C18 column (250×4.6 mm, 5 micron); 1 mL/min flow rate; and eluted with a stepwise gradient: 0-2 min, 95% solvent A and 5% solvent B; 2-32 min 95-65% solvent A and 5-35% solvent B. All $^1$H and $^{13}$C NMR spectra were recorded at 400 MHz (Varian), at room temperature. Spectra were obtained on CDCl$_3$, D$_2$O solutions in 5 mm diameter tubes, and the chemical shift in ppm is quoted relative to the residual signals of CDCl$_3$ ($\delta$H 7.26 ppm, or $\delta$C 77.2 ppm) or D$_2$O ($\delta$H 4.65 ppm). Multiplicities in the $^1$H NMR spectra are described as: s=singlet, d=doublet, t=triplet, q=quartet, m=multiplet, b=broad. All products were characterized by mass spectrometry on a Thermo Electron LTQ-FT mass spectrometer.

Chemical Synthesis

Synthesis of 2-(2-hydroxyethoxy)ethyl 4-nitrobenzenesulfonate (Compound 1)

Figures 1B, 1C:
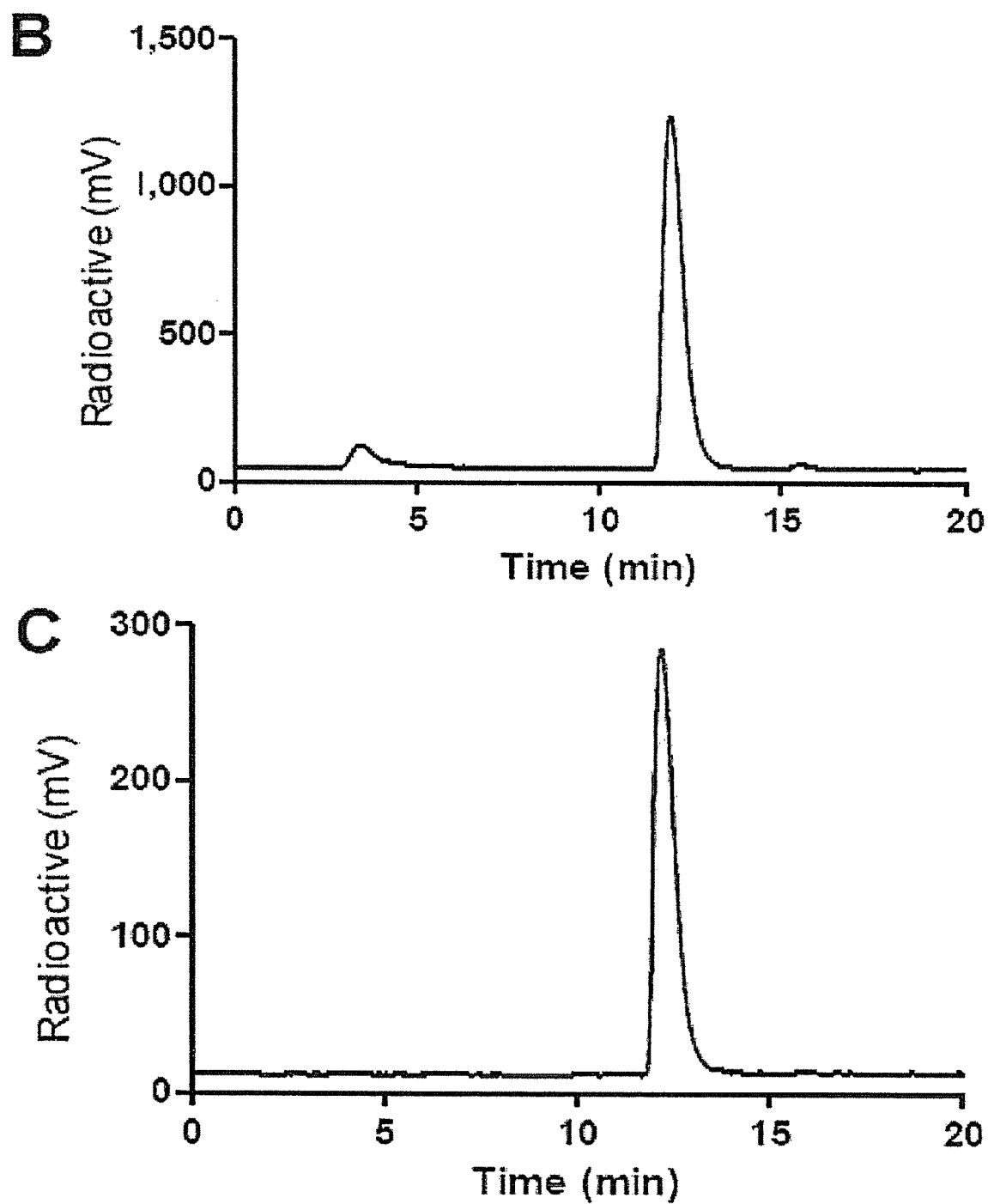

4-Nitrobenzene sulfonyl chloride (12.5 g, 56.6 mmol) was added to a solution of diethylene glycol (5 g, 47 mmol) and triethylamine (9 ml, 66 mmol) in 150 mL of dichloromethane (FIG. 1A). The reaction mixture was stirred at room temperature for overnight, and washed with water and brine. After evaporation of solvent, the residue was purified by column chromatography (dichloromethane/ether, 9:1) to give (1) (yield: 25~30%) as colorless solid. $^1$H-NMR (CDCl$_3$): δ 8.42 (d, 2H), 8.15 (d, 2H), 4.34 (t, 2H), 3.75 (t, 2H), 3.70 (t, 2H), 5.56 (t, 2H). $^{13}$C-NMR (CDCl$_3$): 150.5 (s), 141.9 (s), 129.3 (d), 124.5 (d), 72.6 (t), 70.3 (t), 68.5 (t), 61.7 (t).

Synthesis of 2-(2-(2-(vinylsulfonyl)ethoxy)ethoxy) ethyl 4-nitrobenzenesulfonate (compound 2)

t-BuOK (50 μL, 50% in MeOH) was added to a solution of (1) (1 g, 3.4 mmol) and divinylsulfone (2.2 mL, 20 mmol). The reaction mixture was stirred at room temperature for 4 hr. The reaction mixture was purified by column chromatography (dichloromethane/ether, 9:1) to give (2) (yield: 70-80%) as a colorless solid. $^1$H-NMR (CDCl$_3$): δ 8.41 (d, 2H), 8.13 (d, 2H), 6.78 (d, 1H), 6.41 (d, 1H), 6.11 (d, 1H), 4.29 (t, 2H), 3.88 (t, 2H), 3.72 (t, 2H), 3.58 (s, 4H), 3.24 (t, 2H). 13C-NMR (CDCl$_3$): 150.8 (S), 141.8 (S), 137.9 (d), 129.3 (d), 129.0 (t), 124.5 (d), 70.4 (t), 68.5 (t), 64.6 (t), 54.9 (t).

Synthesis of (2-(2-(2-fluoroethoxy)ethoxy)ethylsulfonyl)ethane ($^{19}$F-DEG-VS, Compound 3)

2-(2-(2-(vinylsulfonyl)ethoxy)ethoxy)ethyl 4-nitrobenzenesulfonate (12 mg, 41.2 μmol) in 50 μL DMSO was added 30 μL TBAF (1M TBAF in THF) and reacted at 78° C. overnight. The reaction mixture was purified on a C18 column on HPLC to give 2.8 mg (3) (yield: 41.3%) as a yellowish liquid. The product was characterized by Thermo LTQ FT mass spectrometer (m/z 227.07 for [MH]$^+$, C$_8$H$_{15}$FO$_4$S, calculated [MH]$^+$ 227.07). 1H-NMR (D$_2$O): δ 6.79 (q, 1H), 6.32 (d, 1H), 6.20 (d, 1H), 4.57 (t, 1H), 4.45 (t, 1H), 3.84 (t, 2H), 3.72 (t, 1H), 3.61 (m, 5H), 3.42 (t, 2H).

Synthesis of $^{19}$F-DEG-VS-cRGDyC cRGDyC (1 mg (1.68 μmol) in 100 μL H$_2$O) and $^{19}$F-DEG-VS (500 μg (2.2 μmol) in 5 μL MeCN and 45 μL H$_2$O) were added into 900 μL of phosphate buffer (pH 7.0). The reaction mixture was incubated at room temperature for 30 min and was purified by HPLC. HPLC conditions: Phenomenex® C18 column; the flow was set at 1 mL/min; and eluent gradient: 0-2 min 95% solvent A [0.1% trifluoroacetic acid (TFA) in water] and 5% solvent B [0.1% TFA in acetonitrile (MeCN)]; 2-7 min 95-85% solvent A and 5-15% solvent B; 7-27 min 85-70% solvent A and 15-30% solvent B. The retention time of $^{19}$F-DEG-VS-cRGDyC was 17.2 min. The final product was a white solid after lyophilization. The product was characterized by Thermo LTQ FT mass spectrometer (m/z 821.29 for [MH]$^+$, C$_{32}$H$_{49}$FN$_8$O$_{12}$S$_2$, calculated [MH]$^+$ 821.29).

Synthesis of $^{19}$F-DEG-VS-cRGDyK cRGDyK (1 mg (1.61 μmol) in 100 μL H$_2$O) and $^{19}$F-DEG-VS (500 μg (2.2 μmol) in 5 μL MeCN and 45 μL H$_2$O) were added into 900 μL of phosphate buffer (pH 9.0). The reaction mixture was incubated at room temperature overnight and was purified by HPLC. The HPLC conditions were the same as the cRGDyK purification. The retention time of $^{19}$F-DEG-VS-cRGDyK was 13.1 min. The final product was a white solid after lyophilization. The product was characterized by Thermo LTQ FT mass spectrometer (m/z 846.38 for [MH]$^+$, C$_{32}$H$_{49}$FN$_8$O$_{12}$S$_2$, calculated [MH]$^+$ 846.38).

Synthesis of $^{19}$F-DEG-VS-Neurotensin and $^{19}$F-DEG-VS-(Ac)-Neurotensin

The neurotensin analog (NT, Cys-pipGly-Pro-pipAmGly-Arg-Pro-Tyr-tBuGly-Leu-OH, 300 μg (0.25 μmol) in 30 μL H$_2$O) or (Ac)-NT and $^{19}$F-DEG-VS (500 μg, 2.2 μmol, 5 μL MeCN and 45 μLH$_2$O) were added into 900 μL of 0.1M borate buffer (pH 8.5). The reaction mixture was incubated at RT for 30 min and purified by HPLC using Method 1. The retention time of $^{19}$F-DEG-VS-NT and ($^{19}$F-DEG-VS)$_2$-NT was 20.08 min and 23.09 min respectively. The final products were white solids after lyophilization. The products were characterized by mass spectrometry ($^{19}$F-DEG-VS-NT: m/z 1,409.75 for [MH]$^+$, $C_{63}H_{105}FN_{16}O_{15}S_2$, calculated [MH]$^+$ 1,409.74; ($^{19}$F-DEG-VS)$_2$-NT: m/z 1,635.82 for [MH]$^+$, $C_{71}H_{120}F_2N_{16}O_{19}S_3$, calculated [MH]$^+$ 1,635.80). The retention time of $^{19}$F-DEG-VS-(Ac)-NT was 28.18 min on radio-HPLC. The final product was confirmed by mass spectrometry ($^{19}$F-DEG-VS-(Ac)-NT: m/z 1,451.76 for [MH]$^+$, $C_{65}H_{108}FN_{16}O_{16}S_2$, calculated [MH]$^+$ 1,451.75.

Synthesis of $^{19}$F-FBEM-c(RGDyC)

FBEM was synthesized as previously described (12). FBEM (420 μg, 1.6 μmol, 50 μL H$_2$O) and c(RGDyC) (500 μg, 0.8 μmol, 50 μL H$_2$O) were added into 200 μL PBS (pH 7.5). The reaction mixture was incubated at RT for 30 min and purified by HPLC using Method 3. The retention time of $^{19}$F-FBEM-c(RGDyC) was 18.2 min. The final product was confirmed by mass spectrometry ($^{19}$F-FBEM-c(RGDyC): m/z 857.30 for [MH]$^+$, $C_{37}H_{45}FN_{10}O_{11}S$, calculated [MH]$^+$ 857.31.

Synthesis of $^{19}$F-FBEM-NT

FBEM (130 μg, 0.5 μmol, 50 μL H$_2$O) and NT (300 μg, 0.25 μmol, 50 μL H$_2$O) were added into 200 μL PBS (pH 7.5). The reaction mixture was incubated at RT for 30 min and purified by HPLC using Method 3. The retention time of $^{19}$F-FBEM-NT was 18.9 min. The final product was confirmed by mass spectrometry ($^{19}$F-FBEM-NT: m/z 1445.74 for [MH]$^+$, $C_{68}H_{101}FN_{18}O_{14}S$, calculated [MH]$^+$ 1445.76.
Radiochemistry Synthesis of $^{18}$F-(2-(2-(2-fluoroethoxy)ethoxy)ethylsulfonyl)ethane ($^{18}$F-DEG-VS, $^{18}$F-3)

$^{18}$F-Fluoride (200 mCi) was trapped onto a Sep-Pak QMA cartridge. Tetrabutylammonium bicarbonate (TBAB) solution (400 μL H$_2$O) was used to elute the $^{18}$F-fluoride from the QMA cartridge into a dried v-vial. The resulting solution was azeotropically dried with sequential MeCN evaporations at 90° C. A solution of (2) (10 mg in 50 μL of anhydrous DMSO) was added to the reactor and heated at 80° C. for 10-15 min. Acetic acid (5%, 800 μL) was added to quench the reaction. The crude mixture was then purified by HPLC (Phenomenex® C18 column: 1 mL/min, and eluent gradient: 0-2 min 95% solvent A and 5% solvent B; 2-7 min 95-85% solvent A and 5-15% solvent B; 7-27 min 85-65% solvent A and 15-35% solvent B. The retention time of $^{19}$F-DEG-VS was 12.2 min. The collected $^{18}$F-DEG-VS was neutralized with NaOH (0.1 mol/L). The isolated radiochemical yield of $^{18}$F-DEG-VS was more than 90% based on HPLC (non-decay-corrected).

Synthesis of $^{18}$F-DEG-VS-cRGDyC $^{18}$F-DEG-VS (100 μL, 1 mCi) and cRGDyC (100 μg) were added into 30 μL of borate buffer (pH 8.5) and the reaction mixture was incubated at room temperature for 5-10 min. The reaction was quenched by acetic acid (5%, 600 μL) and product was purified by HPLC (Phenomenex® C18 column: 1 mL/min, and eluent gradient: 0-2 min 95% solvent A and 5% solvent B; 2-22 min 95-5% solvent A and 5-95% solvent B). The retention time of $^{18}$F-DEG-VS-cRGDyC is 21.5 min.

Synthesis of $^{18}$F-DEG-VS-cRGDyK $^{18}$F-DEG-VS (100 μL, 1 mCi) and 100 μL of borate buffer (pH 9.0) were added into cRGDyK (100 μg) and the reaction mixture was incubated at room temperature for 30 min. The reaction was quenched by acetic acid (5%, 600 μL) and product was purified by HPLC.

Selectivity Test:
cRGDyK and cRGDyC. $^{18}$F-DEG-VS (100 μL, 1 mCi) and 50 μL of borate buffer (pH 8.5) were added into cRGDyC (20 μg) and cRGDyK (20 μg). The reaction mixture was incubated at room temperature for 30 min. The reaction was quenched by acetic acid (5%, 600 μL) and product was purified by HPLC.

Synthesis of $^{18}$F-DEG-VS-NT and $^{18}$F-DEG-VS-(Ac)-NT $^{18}$F-DEG-VS (100 μL, 1 mCi) and 30 μL of borate buffer (pH 8.5) were added into Neurotensin (100 μg, 0.084 μmol) or (Ac)-NT and the reaction mixture was incubated at room temperature for 5-10 min. The reaction was quenched by acetic acid (5%, 600 μL) and product was purified by radio HPLC using Method 1. The retention time of $^{18}$F-DEG-VS-NT was 25.6 min and ($^{18}$F-DEG-VS)$_2$-NT was not observed. In order to study the stability of $^{18}$F-DEG-VS-NT, the final product was incubated with 1×PBS for 5 h at 37° C. An aliquot of the solution was then analyzed by radio-HPLC to determine the radiochemical purify. The retention time of $^{18}$F-DEG-VS-(Ac)-NT was 28.4 min.

Synthesis of $^{18}$F-FBEM-c(RGDyC)

$^{18}$F-FBEM (100 μL, 1 mCi) and 30 μL of PBS (pH 7.5) were added into a vial containing 100 μg c(RGDyC) (0.16 μmol). The reaction mixture was incubated at room temperature for 15 min. The reaction was quenched by acetic acid solution (5%, 600 μL) and the product was purified by radio HPLC using Method 3. The retention time of $^{18}$F-FBEM-c(RGDyC) was 18.4 min.

Synthesis of $^{18}$F-FBEM-NT $^{18}$F-FBEM (100 μL, 1 mCi) and 30 μL of PBS (pH 7.5) were added into a vial containing 100 μg neurotensin peptide (0.084 μmol). The reaction mixture was incubated at room temperature for 15 min. The reaction was quenched by acetic acid solution (5%, 600 μL) and the product was purified by radio HPLC using Method 3. The retention time of $^{18}$F-FBEM-NT was 19.0 min.
Cells The human colon adenocarcinoma cell HT29 was obtained from American Type Culture Collection and maintained at 37° C. in a humidified atmosphere containing 5% CO$_2$ in RPMI-1640, supplemented with 1% L-glutamine, 1% penicillin/streptomycin and 10% fetal bovine serum (Life Technologies, Inc.).
Animals Animal procedures were performed according to a protocol approved by the University of Southern California Institutional Animal Care and Use Committee. In the procedure, 4 to 6 week old, 20 to 30 g, male athymic mice (BALB/c nu/nu) were injected subcutaneously with HT-29 human colon adenocarcinoma cells (American Type Culture Collection) at a concentration of 1×106 cells per 0.1 mL in the shoulder, and enough time was allowed for tumors to grow to at least 3 mm in diameter.
In Vitro Cell Binding Assay The in vitro NTR1-binding affinity and specificity of $^{19}$F-DEG-VS-NT and NT(8-13) were assessed via competitive cell binding assays using $^{125}$I-NT(8-13) (PerkinElmer, Waltham, Mass.) as described previously (18). In detail, HT-29 cells were placed in 48-wells plates (1 million/0.4 mL/well) and were incubated for overnight. The cells were washed three times with binding buffer (50 mM Hepes, 125 mM NaCl, 7.5 mM KCl, 5.5 mM $MgCl_2$, 1 mM EGTA, 5 g/L BSA, 2 mg/L chymostatin, 100 mg/L soybean trypsin inhibitor, 50 mg/L bacitracin, pH 7.4). HT-29 cells were incubated in triplicate with 25000 cpm of $^{125}$I-NT(8-13) and variable concentrations (0.001-1000 nM) of $^{19}$F-DEG-VS-NT and NT(8-13) for 1 hr at 37° C. After washing, cells were solubilized with 1 mol/L NaOH at 37° C. and the radioactivity was determined using a gamma counter. The best-fit 50% inhibitory concentration ($IC_{50}$) values for HT-29 cells were calculated by fitting the data with nonlinear regression using GraphPad Prism (GraphPad Software). Experiments were performed on triplicate samples.

2 Biodistribution and microPET Imaging of HT-29 Tumor Xenografts in Mice.

microPET imaging of were performed in nude mice bearing HT-29 colorectal xenografts after the tail vein injection with 3.7 MBq of $^{18}$F-DEG-VS-NT or $^{18}$F-FBEM-NT (n=3 respectively). For blocking studies, NT(8-13) (100 μg) was co-injected with $^{18}$F-DEG-VS-NT (n=3). Serial imaging (0.5, 1, and 2 hr p.i.; scan duration 5, 5, and 10 min, respectively) was performed using a microPET R4 scanner (Concorde Microsystems, Knoxville, Tenn.; 8 cm axial field of view, spatial resolution 2.0 mm).

Images were reconstructed with a MAP iterative algorithm using the microPET Manager Software (Concorde Microsystems, Knoxville, Tenn.), which Images were then analyzed using the Acquisition Sinogram Image Processing (ASIPro) software (Concorde Microsystems, Knoxville, Tenn.). Average radioactivity accumulation within the liver was obtained from a 3-dimensional region of interest (ROI) drawn within the central portion of the PET liver image. Image intensities were converted to units of activity concentration ($Bq/cm^3$) using a calibration factor obtained by scanning a cylindrical phantom filled with a known activity concentration of $^{18}$F. Assuming a tissue density of 1 g/mL, measured tissue activity concentrations were converted to units of Bq/g, then multiplied by 100 and divided by the injected dose to obtain an image-derived percent injected dose per gram of tissue (% ID/g).

Biodistributions were performed in nude mice bearing HT-29 colorectal xenografts. Animals were sacrificed under inhalation anesthesia at 2 hr post-injection of 3.7 MBq of $^{18}$F-DEG-VS-NT. Tissues and organs of interest were excised and weighed. Radioactivity in each excised specimen was measured using a gamma counter; radioactivity uptake was expressed as % ID/g. Mean uptake (% ID/g) and corresponding standard deviation was calculated for each group of animals.

In Vivo Metabolic Stability.

The in vivo metabolic stability of $^{18}$F-DEG-VS-NT and $^{18}$F-FBEM-NT was evaluated in nude mice bearing HT-29 tumors. Thirty minutes after the intravenous injection of 7.4 MBq of $^{18}$F-DEG-VS-NT or $^{18}$F-FBEM-NT, the mice were sacrificed. Urine was collected and diluted with 1 mL PBS. Blood was centrifuged for 5 min at 14,000 rpm. Liver, kidneys, and tumor were harvested and homogenized using a homogenizer, suspended in 1 mL of PBS buffer, and then centrifuged for 5 min at 14,000 rpm. For each sample, after the removal of the supernatant, 50% TFA in 100 μL PBS was added to the solution, followed by mixing and centrifugation for 5 min. The upper solution was then taken and injected for HPLC analysis (HPLC Method 3). The eluent was collected with a fraction collector (1.0 min/fraction), and the radioactivity of each fraction was measured with a gamma counter. For $^{18}$F-DEG-VS-c(RGDyC) and $^{18}$F-FBEM-c(RGDyC), the urine samples were collected and analyzed by HPLC.

3. Statistical Analysis

Quantitative data were expressed as mean±SD. Means were compared using one-way ANOVA and Student's t test. P values <0.05 were considered statistically significant.

Example 2

Overexpression of neurotensin receptors (NTR) has been associated with both prostate cancer progression and increased growth and proliferation. This work aims to evaluate the PET agent $^{18}$F-DEG-VS-NT for NTR1 targeted imaging of prostate cancer.

The 13-amino acid NT peptide was engineered with a free thiol group (NT-SH) at the amino end. Sulfhydryl specific $^{18}$F-vinyl sulfone ($^{18}$F-VS) was developed for NT-SH conjugation. In vitro studies of $^{18}$F-DEG-VS-NT (including receptor-binding assay, cell uptake, and efflux assay) were conducted using human prostate adenocarcinoma PC3 cell lines. In vivo PET and biodistribution studies were also carried out using nude mice bearing PC3 xenografts.

Starting from azeotropically dried $^{18}$F-fluoride, $^{18}$F-VS was synthesized in a single step with 24.3% decay corrected yield at production scale. The conjugation between NT-SH and $^{18}$F-VS afforded $^{18}$F-DEG-VS-NT in 30.5% isolation yield at room temperature. In the presence of cold NT peptide, the uptake of $^{18}$F-DEG-VS-NT in PC3 cells was successfully blocked. PET imaging analysis demonstrated high tumor uptake, and low background uptake in PC3 tumor model. Biodistribution study was performed at 3 h post injection, which showed the tumor to muscle, liver, and kidney ratios were 19.4±5.5, 15.6±4.1, and 3.0±0.3, respectively.

$^{18}$F-DEG-VS-NT demonstrated high PC3 tumor uptake and low background in normal tissues as shown in microPET images. $^{18}$F-DEG-VS-NT is promising PET agent for prostate cancer diagnosis by targeting NTR1.

Example 3

Based on our newly developed $^{18}$F-vinyl sulfone ($^{18}$F-VS), $^{18}$F-DEG-VS-NT has been developed for neurotensin receptor (NTR) targeted imaging. In this work, we investigate whether this thio-reactive synthon demonstrates benefits compared with the well $^{18}$F-FBEM labeling method.

Based on the well established $^{18}$F-FBEM and our newly developed $^{18}$F-vinyl sulfone, $^{18}$F-FBEM-NT and $^{18}$F-DEG-VS-NT were synthesized for NTR1 targeted imaging. In vivo PET and metabolic stability studies were carried out using nude mice bearing HT29 xenografts.

$^{18}$F-FBEM-NT and $^{18}$F-DEG-VS-NT were obtained in >90% yield based on HPLC integration. Both agents demonstrated good stability in PBS solution. However, the metabolic stability study demonstrated that these agents had several metabolites in vivo, which might due to the very short half life of neurotensin analog. No obvious bone uptake was observed in imaging study indicating in vivo defluorination is neglectable. Although both tracers demonstrated no significant difference in stability studies, $^{18}$F-DEG-VS-NT did have lower abdomen background and higher tumor uptake compared with $^{18}$F-FBEM-NT.

Compared with $^{18}$F-FBEM-NT, $^{18}$F-DEG-VS-NT showed better imaging quality and contrast in in vivo imaging experiment.

Example 4

Neurotensin receptors (NTRs) have been suggested to play key roles in cancer growth and survival. This work aims to develop a $^{18}$F labeled PET agent for NTR1 targeted imaging of various cancer types.

Acetate was introduced to the amino end of CysNT peptide, which was then reacted with $^{18}$F-vinyl sulfone ($^{18}$F-VS). In vivo PET imaging were carried out using nude mice bearing HT29, BXPC3 and Colo205 xenografts.

(Ac)CysNT could react with $^{18}$F-VS efficiently with >90% yield based on HPLC integration. The radiochemical purity of the $^{18}$F-VS-(Ac)NT was >98%. Noninvasive microPET demonstrated that $^{18}$F-VS-(Ac)NT had NTR-specific tumor uptake in subcutaneous HT-29, BXPC3, and Colo205 xenografts. Receptor specificity was successfully demonstrated by blocking experiment.

$^{18}$F-VS-(Ac)NT demonstrated specific tumor uptake and good tumor to background contrast in colorectal and pancreatic cancer models. $^{18}$F-VS-(Ac)NT is a promising agent for NTR1 targeted PET imaging.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

TABLE 1

Selected conditions for the radiosynthesis of $^{18}$F-DEG-VS

| Precursor amount | Reaction temperature | Radiochemical yield (Based on HPLC) |
|---|---|---|
| 2 mg | 80° C. | >75% |
| 10 mg | 80° C. | >90% |
| 20 mg | 80° C. | >95% |
| 20 mg | 60° C. | >95% |

REFERENCES

The following references are each relied upon and incorporated herein in their entirety 1. Li Z, Conti P S. Radiopharmaceutical chemistry for positron emission tomography. Adv Drug Deliv Rev. 2010; 62(11):1031-1051.
2. Wester H J, Hamacher K, Stocklin G. A comparative study of N.C.A. fluorine-18 labeling of proteins via acylation and photochemical conjugation. Nucl Med Biol. 1996; 23(3):365-372.
3. Vaidyanathan G, Zalutsky M R. Synthesis of N-succinimidyl 4-[18F]fluorobenzoate, an agent for labeling proteins and peptides with 18F. Nat Protoc. 2006; 1(4):1655-1661.
4. Kuchar M, Pretze M, Kniess T, et al. Site-selective radiolabeling of peptides by 18F-fluorobenzoylation with [18F]SFB in solution and on solid phase: a comparative study. Amino Acids. 2012; 43(4):1431-1443.
5. Sykes T R, Ruth T J, Adam M J. Synthesis and murine tissue uptake of sodium [18F]fluoroacetate. Int J Rad Appl Instrum B. 1986; 13(5):497-500.
6. Sun L Q, Mori T, Dence C S, et al. New approach to fully automated synthesis of sodium [18F]fluoroacetate—a simple and fast method using a commercial synthesizer. Nucl Med Biol. 2006; 33(1):153-158.
7. Block D, Coenen H H, Stöcklin G. N.C.A. 18F-fluoroacylation via fluorocarboxylic acid esters. J Label Compd Radiopharm. 1988; 25(2):185-200.
8. Lang L, Eckelman W C. Labeling proteins at high specific activity using N-succinimidyl 4-[18F](fluoromethyl)benzoate. Appl Radiat Isot. 1997; 48(2):169-173.
9. Aloj L, Lang L, Jagoda E, et al. Evaluation of human transferrin radio-labeled with N-succinimidyl 4-[fluorine-18](fluoromethyl)benzoate. J Nucl Med. 1996; 37(8):1408-1412.
10. Kilbourn M R, Dence C S, Welch M J, et al. Fluorine-18 labeling of proteins. J Nucl Med. 1987; 28(4):462-470.
11. Shiue C Y, Wolf A P, Hainfeld J F. Synthesis of 18F-labelled N-(p-[18F]fluorophenyl)maleimide and its derivatives for labelling monoclonal antibody with 18F. Journal of Labelled Compounds and Radiopharmaceuticals. 1989; 26(1-12):287-289.
12. Toyokuni T, Walsh J C, Dominguez A, et al. Synthesis of a new heterobifunctional linker, N-[4-(aminooxy)butyl]maleimide, for *facile* access to a thiol-re active 18F-labeling agent. Bioconjug Chem. 2003; 14(6):1253-1259.
13. Hansen C L, Kuhnast B, Hinnen F, et al. Comparison of [18F]FBA and [18F]FPyMe as peptide radiolabeling agents of PEPHC1 for PET imaging of EGFRvIII. Adv Exp Med Biol. 2009; 611:405-406.
14. Cai W, Zhang X, Wu Y, et al. A thiol-reactive 18F-labeling agent, N-[2-(4-18F-fluorobenzamido)ethyl]maleimide, and synthesis of RGD peptide-based tracer for PET imaging of alpha v beta 3 integrin expression. J Nucl Med. 2006; 47(7):1172-1180.
15. Morales-Sanfrutos J, Lopez-Jaramillo J, Ortega-Munoz M, et al. Vinyl sulfone: a versatile function for simple bioconjugation and immobilization. Org Biomol Chem. 2010; 8(3):667-675.
16. Vincent J P, Mazella J, Kitabgi P. Neurotensin and neurotensin receptors. Trends Pharmacol Sci. 1999; 20(7):302-309.
17. Myers R M, Shearman J W, Kitching M O, et al. Cancer, chemistry, and the cell: molecules that interact with the neurotensin receptors. ACS Chem Biol. 2009; 4(7):503-525.
18. Garcia-Garayoa E, Allemann-Tannahill L, Blauenstein P, et al. In vitro and in vivo evaluation of new radiolabeled neurotensin(8-13) analogues with high affinity for NT1 receptors. Nucl Med Biol. 2001; 28(1):75-84.
19. Moody T W, Chan D, Fahrenkrug J, et al. Neuropeptides as autocrine growth factors in cancer cells. Curr Pharm Des. 2003; 9(6):495-509.
20. Reubi J C, Waser B, Friess H, et al. Neurotensin receptors: a new marker for human ductal pancreatic adenocarcinoma. Gut. 1998; 42(4):546-550.
21. Souaze F, Dupouy S, Viardot-Foucault V, et al. Expression of neurotensin and NT1 receptor in human breast cancer: a potential role in tumor progression. Cancer Res. 2006; 66(12):6243-6249.
22. Reubi J C, Macke H R, Krenning E P. Candidates for peptide receptor radiotherapy today and in the future. J Nucl Med. 2005; 46 Suppl 1:67S-75S.
23. Somai S, Gompel A, Rostene W, et al. Neurotensin counteracts apoptosis in breast cancer cells. Biochem Biophys Res Commun. 2002; 295(2):482-488.
24. Reubi J C, Waser B, Schaer J C, et al. Neurotensin receptors in human neoplasms: high incidence in Ewing's sarcomas. Int J Cancer. 1999; 82(2):213-218.
25. Bunn P A, Jr., Dienhart D G, Chan D, et al. Effects of neuropeptides on human lung and breast cancer cells. J Natl Cancer Inst Monogr. 1992(13):145-151.

26. Dupouy S, Mourra N, Doan V K, et al. The potential use of the neurotensin high affinity receptor 1 as a biomarker for cancer progression and as a component of personalized medicine in selective cancers. Biochimie. 2011; 93(9):1369-1378.
27. Goedert M, Reeve J G, Emson P C, et al. Neurotensin in human small cell lung carcinoma. Br J Cancer. 1984; 50(2):179-183.
28. Alifano M, Souaze F, Dupouy S, et al. Neurotensin receptor 1 determines the outcome of non-small cell lung cancer. Clin Cancer Res. 2010; 16(17):4401-4410.
29. Bergmann R, Scheunemann M, Heichert C, et al. Biodistribution and catabolism of 18F-labeled neurotensin(8-13) analogs. Nucl Med Biol. 2002; 29(1):61-72.
30. Teodoro R, Faintuch B L, Nunez E G, et al. Neurotensin (8-13) analogue: radiolabeling and biological evaluation using different chelators. Nucl Med Biol. 2011; 38(1): 113-120.
31. Buchegger F, Bonvin F, Kosinski M, et al. Radiolabeled neurotensin analog, 99mTc-NT-XI, evaluated in ductal pancreatic adenocarcinoma patients. J Nucl Med. 2003; 44(10:1649-1654.
32. Zhang K, An R, Gao Z, et al. Radionuclide imaging of small-cell lung cancer (SCLC) using 99mTc-labeled neurotensin peptide 8-13. Nucl Med Biol. 2006; 33(4):505-512.
33. Garcia-Garayoa E, Blauenstein P, Blanc A, et al. A stable neurotensin-based radiopharmaceutical for targeted imaging and therapy of neurotensin receptor-positive tumours. Eur J Nucl Med Mol Imaging. 2009; 36(1):37-47.
34. de Visser M, Janssen P J, Srinivasan A, et al. Stabilised 111In-labelled DTPA- and ROTA-conjugated neurotensin analogues for imaging and therapy of exocrine pancreatic cancer. Eur J Nucl Med Mol Imaging. 2003; 30(8):1134-1139.
35. Alshoukr F, Prignon A, Brans L, et al. Novel DOTA-neurotensin analogues for 111In scintigraphy and 68Ga PET imaging of neurotensin receptor-positive tumors. Bioconjug Chem. 2011; 22(7):1374-1385.
36. Wu Z, Todorov I, Li L, et al. In vivo imaging of transplanted islets with 64Cu-DO3A-VS-Cys40-Exendin-4 by targeting GLP-1 receptor. Bioconjug Chem. 2011; 22(8):1587-1594.
37. Wu Z, Liu S, Hassink M, et al. Development and Evaluation of 18F-TTCO-Cys40-Exendin-4: A PET Probe for Imaging Transplanted Islets. J Nucl Med. 2013; 54(2):244-251.

What is claimed is:

1. A thio-selective radioactive labeling agent comprising a conjugate having the formula *R-L-VS, wherein a radioisotope, *R, is conjugated to a linking group L, and the linking group is conjugated to a vinylsulfone functional group VS, wherein *R is $^{18}F$, and the linking group, L, comprises diethylene glycol, wherein the vinylsulfone functional group VS has the structure:

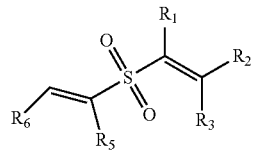

wherein $R_1$, $R_2$, and $R_3$ are independently selected from the group consisting of H, alkyl, cycloalkyl, aryl, and heteroaryl, wherein $R_1$ and $R_2$ may be optionally substituted so as to form a $C_3$-$C_8$ cyclic unsaturated ring and the selected alkyl, cycloalkyl, aryl and heteroaryls may be optionally substituted, and wherein $R_5$ and $R_6$ are independently selected from the group consisting of H, alkyl, cycloalkyl, aryl, and heteroaryl.

2. The thio-selective radioactive labeling agent of claim 1, wherein $R_1$, $R_2$, and $R_3$ are independently selected from the group consisting of H, alkyl, cycloalkyl, aryl, and heteroaryl, and wherein $R_1$ and $R_2$ are substituted so as to form a $C_3$-$C_8$ cyclic unsaturated ring and the selected alkyl, cycloalkyl, aryl and heteroaryls may be optionally substituted.

3. The thio-selective radioactive labeling agent of claim 2, wherein $R_1$ and $R_2$ are substituted so as to form a $C_3$-$C_8$ cyclic unsaturated ring and the selected alkyl, aryl and heteroaryls are substituted.

4. The thio-selective radioactive labeling agent of claim 1, wherein the vinylsulfone functional group VS has the structure:

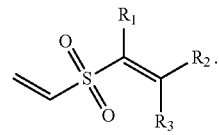

5. The thio-selective radioactive labeling agent of claim 4, wherein $R_1$ and $R_2$ are substituted so as to form a $C_3$-$C_8$ cyclic unsaturated ring and the selected alkyl, cycloalkyl, aryl and heteroaryls may be optionally substituted.

6. The thio-selective radioactive labeling agent of claim 4, wherein the vinylsulfone functional group VS has the structure:

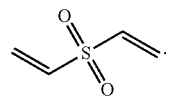

* * * * *